(12) United States Patent
Redington

(10) Patent No.: US 10,136,895 B2
(45) Date of Patent: Nov. 27, 2018

(54) USE OF REMOTE ISCHEMIC CONDITIONING TO IMPROVE OUTCOME AFTER MYOCARDIAL INFARCTION

(71) Applicant: The Hospital for Sick Children, Toronto (CA)

(72) Inventor: Andrew Redington, Cincinnati, OH (US)

(73) Assignee: The Hospital for Sick Children, Toronto (CA)

( * ) Notice: Subject to any disclaimer, the term of this patent is extended or adjusted under 35 U.S.C. 154(b) by 300 days.

(21) Appl. No.: 14/744,665

(22) Filed: Jun. 19, 2015

(65) Prior Publication Data

US 2016/0038147 A1  Feb. 11, 2016

Related U.S. Application Data

(62) Division of application No. 13/021,649, filed on Feb. 4, 2011, now abandoned.

(60) Provisional application No. 61/319,597, filed on Mar. 31, 2010.

(51) Int. Cl.
| | |
|---|---|
| *A61B 17/12* | (2006.01) |
| *A61B 17/132* | (2006.01) |
| *A61B 17/135* | (2006.01) |
| *A61B 17/00* | (2006.01) |
| *A61K 31/00* | (2006.01) |

(52) U.S. Cl.
CPC .... *A61B 17/12009* (2013.01); *A61B 17/1327* (2013.01); *A61B 17/1355* (2013.01); *A61B 2017/00199* (2013.01); *A61B 2017/00544* (2013.01); *A61K 31/00* (2013.01)

(58) Field of Classification Search
CPC .......... A61B 17/12009; A61B 17/1355; A61B 17/1327; A61B 2017/00199; A61B 2017/00544
See application file for complete search history.

(56) References Cited

U.S. PATENT DOCUMENTS

| | | | |
|---|---|---|---|
| 3,552,383 | A | 1/1971 | Krueger et al. |
| 4,106,002 | A | 8/1978 | Hogue, Jr. |
| 4,206,764 | A | 6/1980 | Williams |
| 4,321,929 | A | 3/1982 | Lemelson et al. |
| 4,664,651 | A | 5/1987 | Weinshenker et al. |
| 5,092,317 | A | 3/1992 | Zelikovski |
| 5,135,003 | A | 8/1992 | Souma |
| 5,267,565 | A | 12/1993 | Beard et al. |
| 5,569,304 | A | 10/1996 | Ulrich |

(Continued)

FOREIGN PATENT DOCUMENTS

| | | |
|---|---|---|
| CA | 2692463 A1 | 1/2009 |
| CN | 201098315 Y | 8/2008 |

(Continued)

OTHER PUBLICATIONS

Examination Report for Application No. AU2011234189 dated Mar. 31, 2015.

(Continued)

*Primary Examiner* — Howie Matthews
(74) *Attorney, Agent, or Firm* — Wolf, Greenfield & Sacks, P.C.

(57) ABSTRACT

The invention provides methods for reducing the incidence and/or severity and/or delaying the onset of heart dysfunction/failure and improving overall survival through the use of remote ischemic per-conditioning and post-conditioning.

25 Claims, 15 Drawing Sheets
Specification includes a Sequence Listing.

(56) References Cited

U.S. PATENT DOCUMENTS

| | | |
|---|---|---|
| 5,571,075 A | 11/1996 | Bullard et al. |
| 5,634,467 A | 6/1997 | Nevo |
| 5,651,369 A | 7/1997 | Tomita |
| 6,020,334 A | 2/2000 | Fukushi et al. |
| 6,149,618 A | 11/2000 | Sato |
| 6,152,881 A | 11/2000 | Raines et al. |
| 6,210,423 B1 | 4/2001 | Kim et al. |
| 6,303,649 B1 | 10/2001 | Hattori et al. |
| 6,485,429 B2 | 11/2002 | Forstner |
| 6,550,482 B1 | 4/2003 | Burbank et al. |
| 6,626,840 B2 | 9/2003 | Drzewiecki et al. |
| 6,660,759 B1 | 12/2003 | Hattori et al. |
| 6,670,362 B2 | 12/2003 | Banks et al. |
| 6,702,720 B2 | 3/2004 | Dardik |
| 6,719,704 B2 | 4/2004 | Narimatsu et al. |
| 6,858,012 B2 | 2/2005 | Burns et al. |
| 6,962,599 B2 | 11/2005 | Hui et al. |
| 7,004,907 B2 | 2/2006 | Banet et al. |
| 7,018,335 B2 | 3/2006 | Kario et al. |
| 7,048,702 B2 | 5/2006 | Hui |
| 7,314,478 B2 | 1/2008 | Hui |
| 7,338,410 B2 | 3/2008 | Dardik et al. |
| 7,374,540 B2 | 5/2008 | Schnall et al. |
| 7,390,303 B2 | 6/2008 | Dafni |
| 7,517,312 B2 | 4/2009 | Loeb et al. |
| 7,615,548 B2 | 11/2009 | Gottlieb et al. |
| 7,635,722 B1 | 12/2009 | Bachynsky et al. |
| 7,689,286 B2 | 3/2010 | Pastore et al. |
| 7,717,855 B2 | 5/2010 | Caldarone et al. |
| 8,114,026 B2 | 2/2012 | Leschinsky |
| 8,246,548 B2 | 8/2012 | Naghavi et al. |
| 8,764,789 B2 | 7/2014 | Ganske et al. |
| 8,790,266 B2 | 7/2014 | Caldarone et al. |
| 8,911,469 B2 | 12/2014 | Raheman |
| 2001/0029389 A1 | 10/2001 | Kim et al. |
| 2003/0013974 A1 | 1/2003 | Natarajan et al. |
| 2003/0065270 A1 | 4/2003 | Raines et al. |
| 2003/0143662 A1 | 7/2003 | Cummings et al. |
| 2003/0176795 A1 | 9/2003 | Harris et al. |
| 2003/0216651 A1 | 11/2003 | Burns et al. |
| 2003/0233118 A1 | 12/2003 | Hui |
| 2004/0044290 A1 | 3/2004 | Ward et al. |
| 2004/0064076 A1 | 4/2004 | Bilgi et al. |
| 2004/0102818 A1 | 5/2004 | Hakky et al. |
| 2004/0134492 A1 | 7/2004 | Dardik |
| 2004/0241634 A1 | 12/2004 | Millis et al. |
| 2004/0255956 A1 | 12/2004 | Vinten-Johansen |
| 2005/0004476 A1 | 1/2005 | Payvar et al. |
| 2005/0070405 A1 | 3/2005 | Egger |
| 2005/0159640 A1 | 7/2005 | Barbut et al. |
| 2005/0177078 A1 | 8/2005 | Loeb et al. |
| 2006/0024779 A1 | 2/2006 | Cummings et al. |
| 2006/0052712 A1 | 3/2006 | Poliac et al. |
| 2006/0052713 A1 | 3/2006 | Poliac et al. |
| 2006/0052714 A1 | 3/2006 | Poliac et al. |
| 2006/0058717 A1 | 3/2006 | Hui et al. |
| 2006/0100639 A1 | 5/2006 | Levin et al. |
| 2006/0122544 A1 | 6/2006 | Ciluffo |
| 2006/0142663 A1 | 6/2006 | Sawanoi et al. |
| 2006/0167390 A1 | 7/2006 | Hui |
| 2007/0150005 A1 | 6/2007 | Sih et al. |
| 2007/0179421 A1 | 8/2007 | Farrow |
| 2008/0097385 A1 | 4/2008 | Vinten-Johansen et al. |
| 2008/0119904 A1 | 5/2008 | Salo et al. |
| 2008/0139949 A1 | 6/2008 | Caldarone et al. |
| 2008/0222769 A1 | 9/2008 | Natonson et al. |
| 2009/0137884 A1 | 5/2009 | Naghavi et al. |
| 2009/0221649 A1 | 9/2009 | Krahn et al. |
| 2009/0238852 A1 | 9/2009 | Kennedy et al. |
| 2009/0287069 A1 | 11/2009 | Naghavi et al. |
| 2009/0324748 A1 | 12/2009 | Dobson |
| 2010/0081941 A1 | 4/2010 | Naghavi et al. |
| 2010/0105993 A1 | 4/2010 | Naghavi et al. |
| 2010/0160444 A1 | 6/2010 | Gottlieb et al. |
| 2010/0160799 A1 | 6/2010 | Caldarone et al. |
| 2010/0185220 A1 | 7/2010 | Naghavi et al. |
| 2010/0292619 A1 | 11/2010 | Redington et al. |
| 2010/0305607 A1 | 12/2010 | Caldarone et al. |
| 2010/0322467 A1 | 12/2010 | Reed et al. |
| 2010/0324429 A1 | 12/2010 | Leschinsky |
| 2010/0328142 A1 | 12/2010 | Zoughi et al. |
| 2011/0190807 A1 | 8/2011 | Redington et al. |
| 2011/0208099 A1 | 8/2011 | Naghavi et al. |
| 2011/0224606 A1 | 9/2011 | Shome et al. |
| 2011/0251635 A1 | 10/2011 | Caldarone |
| 2011/0319732 A1 | 12/2011 | Naghavi et al. |
| 2012/0130419 A1 | 5/2012 | Leschinsky |
| 2012/0265240 A1 | 10/2012 | Ganske et al. |
| 2012/0277789 A1 | 11/2012 | Caldarone et al. |
| 2013/0317581 A1 | 11/2013 | Redington |
| 2014/0296756 A1 | 10/2014 | Ganske et al. |

FOREIGN PATENT DOCUMENTS

| | | |
|---|---|---|
| CN | 200820123637 | 11/2008 |
| CN | 101317805 A | 12/2008 |
| CN | 201316381 Y | 9/2009 |
| EP | 0 960 598 A1 | 12/1999 |
| EP | 1 249 218 A2 | 10/2002 |
| JP | 07-051276 | 2/1995 |
| JP | 2001505472 A | 4/2001 |
| JP | 2002539879 A | 11/2002 |
| RU | 2 253 429 C1 | 6/2005 |
| WO | WO 83/00995 A1 | 3/1983 |
| WO | WO 98/30144 A1 | 7/1998 |
| WO | WO 00/57776 A1 | 10/2000 |
| WO | WO 2004/004702 A2 | 1/2004 |
| WO | WO 2005/011503 A1 | 2/2005 |
| WO | WO 2005/077265 A1 | 8/2005 |
| WO | WO 2006/024871 A1 | 3/2006 |
| WO | WO 2006/030441 A2 | 3/2006 |
| WO | WO 2006/061825 A2 | 6/2006 |
| WO | WO 2006/069170 A2 | 6/2006 |
| WO | WO 2006/099958 A1 | 9/2006 |
| WO | WO 2008/148045 A1 | 12/2008 |
| WO | WO 2008/148062 A1 | 12/2008 |
| WO | WO 2011/005538 A2 | 1/2011 |
| WO | WO 2012/016280 A1 | 2/2012 |

OTHER PUBLICATIONS

Leconte et al., Delayed hypoxic postconditioning protects against cerebral ischemia in the mouse. Stroke. Oct. 2009;40(10):3349-55. doi: 10.1161/STROKEAHA.109.557314. Epub Jul. 23, 2009.

Ren et al., Limb remote ischemic postconditioning protects against focal ischemia in rats. Brain Res. Sep. 8, 2009;1288:88-94. doi: 10.1016/j.brainres.2009.07.029. Epub Jul. 23, 2009.

Toledo-Pereyra et al., Molecular signaling pathways in ischemia/reperfusion. Exp Clin Transplant. Jun. 2004;2(1):174-7.

Zhao, Ischemic postconditioning as a novel avenue to protect against brain injury after stroke. J Cereb Blood Flow Metab. May 2009;29(5):873-85. doi: 10.1038/jcbfm.2009.13. Epub Feb. 25, 2009.

Liu et al., Remote ischemic postconditioning promotes the survival of retinal ganglion cells after optic nerve injury. J Mol Neurosci. Nov. 2013;51(3):639-46. doi: 10.1007/s12031-013-0036-2. Epub Jun. 5, 2013.

Slepian et al., Pre-conditioning of smooth muscle cells via induction of the heat shock response limits proliferation following mechanical injury. Biochem Biophys Res Commun. Aug. 14, 1996;225(2):600-7.

Tanaka et al., Expression of heat shock protein after ischemic preconditioning in rabbit hearts. Jpn Circ J. Jul. 1998;62(7):512-6.

Kin et al., Post-Conditioning attenuates myocardial ischemia-reperfusion injury by inhibiting events in the early minutes of reperfusion, Cardiovascular Research, vol. 62, pp. 74-85 (2004).

Pasupathy et al., Ischaemic preconditioning protects against ischaemia/reperfusion injury: emerging concepts. Eur J Vasc Endovasc Surg. Feb. 2005;29(2):106-15.

(56) References Cited

OTHER PUBLICATIONS

Thielmann et al., Remote ischemic preconditioning: the surgeon's perspective. J Cardiovasc Med (Hagerstown). Oct. 1, 2012;13:1-6 [Epub ahead of print].
Ali et al., Remote ischemic preconditioning reduces myocardial and renal injury after elective abdominal aortic aneurysm repair: a randomized controlled trial. Circulation. Sep. 11, 2007;116(11 Suppl):198-105.
Bartekova et al., Liver ischemia induced remote preconditioning: role of cardioprotective proteins. 25. ISHR-ES meeting. Jun. 21-25, 2005. Tromsoe, Norway. J Mol Cell Cardiol. 2005;38(6):1004.
Bøtker et al., Upper-limb ischemia during ambulance transfer reduces myocardial perfusion injury in STEMI. Heartwire. Mar. 28, 2009. Featured at i2 Session of AAC. Mar. 28-31, 2009. Last Accessed on Mar. 5, 2012 from http://www.theheart.org/article/951627.do.
Bøtker et al., Remote ischaemic conditioning before hospital admission, as a complement to angioplasty, and effect on myocardial salvage in patients with acute myocardial infarction: a randomised trial. Lancet. Feb. 27, 2010;375(9716):727-34.
Brzozowski et al., Ischemic preconditioning of remote organs attenuates gastric ischemia-reperfusion injury through involvement of prostaglandins and sensory nerves. Eur J Pharmacol. Sep. 19, 2004;499(1-2):201-13.
Cheung et al., Randomized controlled trial of the effects of remote ischemic preconditioning on children undergoing cardiac surgery: first clinical application in humans. J Am Coll Cardiol. Jun. 6, 2006,47(11):2277-82.
Dickson et al., Rabbit heart can be "preconditioned" via transfer of coronary effluent. Am J Physiol. Dec. 1999;277(6 Pt 2):H2451-7.
Dong et al., Limb ischemic preconditioning reduces infarct size following myocardial ischemia-reperfusion in rats] Sheng Li Xue Bao. Feb. 25, 2004;56(1):41-6. Chinese.
Gho et al., Myocardial protection by brief ischemia in noncardiac tissue. Circulation. Nov. 1, 1996;94(9):2193-200.
Hausenloy et al., Effect of remote ischaemic preconditioning on myocardial injury in patients undergoing coronary artery bypass graft surgery: a randomised controlled trial. Lancet. Aug. 18, 2007;370(9587):575-9.
Hausenloy et al., Preconditioning and postconditioning: underlying mechanisms and clinical application. Atherosclerosis. Jun. 2009;204(2):334-41. Epub Nov. 5, 2008.
Hausenloy et al., The therapeutic potential of ischemic conditioning: an update. Nat Rev Cardiol. Jun. 21, 2011;8(11):619-29.
Hoole et al., Cardiac Remote Ischemic Preconditioning in Coronary Stenting (CRISP Stent) Study: a prospective, randomized control trial. Circulation. Feb. 17, 2009;119(6):820-7. Epub Feb. 2, 2009.
Jenkins et al., Ischaemic preconditioning reduces troponin T release in patients undergoing coronary artery bypass surgery. Heart. Apr. 1997;77(4):314-8.
Kerendi et al., Remote postconditioning. Brief renal ischemia and reperfusion applied before coronary artery reperfusion reduces myocardial infarct size via endogenous activation of adenosine receptors. Basic Res Cardiol. Sep. 2005;100(5):404-12. Epub Jun. 17, 2005.
Kharbanda et al., Ischemic preconditioning prevents endothelial injury and systemic neutrophil activation during ischemia-reperfusion in humans in vivo. Circulation. Mar. 27, 2001;103(12):1624-30.
Kharbanda et al., Remote ischaemic preconditioning protects against cardiopulmonary bypass-induced tissue injury: a preclinical study. Heart. Oct. 2006;92(10):1506-11. Epub Jul. 3, 2006.
Kharbanda et al., Transient limb ischemia induces remote ischemic preconditioning in vivo. Circulation. Dec. 3, 2002;106(23):2881-3.
Kin et al., Postconditioning attenuates myocardial ischemia-reperfusion injury by inhibiting events in the early minutes of reperfusion. Cardiovasc Res. Apr. 1, 2004,62(1):74-85.
Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.
Konstantinov et al., The remote ischemic preconditioning stimulus modifies inflammatory gene expression in humans. Physiol Genomics. Sep. 16, 2004;19(1):143-50. Epub Aug. 10, 2004.
Konstantinov et al., The remote ischemic preconditioning stimulus modifies gene expression in mouse myocardium. J Thorac Cardiovasc Surg. Nov. 2005;130(5):1326-32.
Lang et al., Myocardial preconditioning and remote renal preconditioning—identifying a protective factor using proteomic methods? Basic Res Cardiol. Mar. 2006;101(2):149-58. Epub Nov. 11, 2005.
Laskey et al., Frequency and clinical significance of ischemic preconditioning during percutaneous coronary intervention. J Am Coll Cardiol. Sep. 17, 2003;42(6):998-1003.
Leesar et al., Nonelectrocardiographic evidence that both ischemic preconditioning and adenosine preconditioning exist in humans. J Am Coll Cardiol. Aug. 6, 2003;42(3):437-45.
Leesar et al., Preconditioning of human myocardium with adenosine during coronary angioplasty. Circulation. Jun. 3, 1997;95(11):2500-7.
Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.
McCully et al., Adenosine-enhanced ischemic preconditioning: adenosine receptor involvement during ischemia and reperfusion. Am J Physiol Heart Circ Physiol. Feb. 2001;280(2):H591-602.
Murry et al., Preconditioning with ischemia: a delay of lethal cell injury in ischemic myocardium. Circulation. Nov. 1986;74(5):1124-36.
Nandagopal et al., Critical role for nitric oxide signaling in cardiac and neuronal ischemic preconditioning and tolerance. *J Pharmacol Exp Ther.* May 2001;297(2):474-8.
Peng et al., The protective effects of ischemic and calcitonin gene-related peptide-induced preconditioning on myocardial injury by endothelin-1 in the isolated perfused rat heart. Life Sci. 1996;59(18):1507-14.
Penttila et al., Ischemic preconditioning does not improve myocardial preservation during off-pump multivessel coronary operation. Ann Thorac Surg. Apr. 2003;75(4):1246-52; discussion 1252-3.
Peralta et al., Liver ischemic preconditioning: a new strategy for the prevention of ischemia-reperfusion injury. Transplant Proc. Aug. 2003;35(5):1800-2.
Przyklenk et al., Regional ischemic 'preconditioning' protects remote virgin myocardium from subsequent sustained coronary occlusion. Circulation. Mar. 1993;87(3):893-9.
Schipke et al., [Postconditioning: a brief review]. Herz. Sep. 2006;31(6):600-6. Review. German. Abstract.
Schmidt et al., Intermittent peripheral tissue ischemia during coronary ischemia reduces myocardial infarction through a KATP-dependent mechanism: first demonstration of remote ischemic perconditioning. Am J Physiol Heart Circ Physiol. Apr. 2007;292(4):H1883-90. Epub Dec. 15, 2006.
Schoemaker et al., Bradykinin mediates cardiac preconditioning at a distance. Am J Physiol Heart Circ Physiol. May 2000;278(5):H1571-6.
Sun et al., Postconditioning attenuates cardiomyocyte apoptosis via inhibition of JNK and p38 mitogen-activated protein kinase signaling pathways. Apoptosis. Sep. 2006;11(9):1583-93.
Tomai et al., Ischemic preconditioning in humans: models, mediators, and clinical relevance. Circulation. Aug. 3, 1999;100(5):559-63.
Vinten-Johansen et al., Postconditioning—A new link in nature's armor against myocardial ischemia-reperfusion injury. Basic Res Cardiol. Jul. 2005;100(4):295-310. Epub Mar. 30, 2005.
Wolfrum et al., Calcitonin gene related peptide mediates cardioprotection by remote preconditioning. Regul Pept. Apr. 15, 2005;127(1-3):217-24.
Zhang et al., [Correlation of limb and myocardial ischemia postconditioning with acute myocardial reperfusion injury]. Zhonghua Yi Xue Za Zhi. Mar. 28, 2006;86(12):841-5. Chinese. (Abstract Only).

(56) References Cited

OTHER PUBLICATIONS

Zhao et al., Inhibition of myocardial injury by ischemic postconditioning during reperfusion: comparison with ischemic preconditioning. Am J Physiol Heart Circ Physiol. Aug. 2003;285(2):H579-88.
Ali et al., Induced remote ischemic pre-conditioning on ischemia-reperfusion injury in patients undergoing coronary artery bypass. J Coll Physicians Surg Pak. Jul. 2010;20(7):427-431.
Andreka et al., Remote ischaemic postconditioning protects the heart during acute myocardial infarction in pigs. Heart. Jun. 2007;93(6):749-52. Epub Apr. 20, 2007.
Bauer et al., Does preconditioning protect the coronary vasculature from subsequent ischemia/reperfusion injury? Circulation. Aug. 1993;88(2):659-72.
Bell, Remote ischaemic conditioning and ischaemic heart disease. Br J Hosp Med (Loud). Jan. 2014;75(1):C13-6.
Birnbaum et al., Ischemic preconditioning at a distance:reduction of myocardial infarct size by partial reduction of blood supply combined with rapid stimulation of the gastrocnemius muscle in the rabbit. Circulation. Sep. 2, 1997;96(5):1641-6.
Bøtker et al., Prehospital remote ischemic preconditioning reduces infarct size in patients with evolving myocardial infarction undergoing primary percutaneous intervention. Fondation Leducq Transatlantic Network Presentation. Mar. 2009. 23 pgs.
Choi et al., Effect of remote ischemic preconditioning on renal dysfunction after complex valvular heart surgery: A randomized controlled trial. J Thorac Cardiovasc Surg. 2011;142:148-154.
Crimi et al., Remote ischemic post-conditioning of the lower limb during primary percutaneous coronary intervention safely reduces enzymatic infarct size in anterior myocardial infarction: a randomized controlled trial. JACC Cardiovasc Interv. Oct. 2013;6(10):1055-63.
D'Ascenzo et al., Remote ischaemic preconditioning in coronary artery bypass surgery: a meta-analysis. Heart. Sep. 2012;98(17):1267-71.
D'Ascenzo et al., Cardiac remote ischaemic preconditioning reduces periprocedural myocardial infarction for patients undergoing percutaneous coronary interventions: a meta-analysis of randomised clinical trials. EuroIntervention. Apr. 2014;9(12):1463-71. doi: 10.4244/EIJV9I12A244.
Dave et al., Remote organ ischemic preconditioning protect brain from ischemic damage following asphyxial cardiac arrest. Neurosci Lett. Aug. 14, 2006;404(1-2):170-5. Epub Jun. 15, 2006.
Ghaemian et al., Remote ischemic preconditioning in percutaneous coronary revascularization: a double-blind randomized controlled clinical trial. Asian Cardiovasc Thorac Ann. Oct. 2012;20(5):548-54.
Gritsopoulos et al., Remote postconditioning is more potent than classic postconditioning in reducing the infarct size in anesthetized rabbits. Cardiovasc Drugs Ther. Jun. 2009;23(3):193-8. Abstract.
Gurusamy et al., Ischaemic preconditioning for liver transplantation. Cochrane Database Syst Rev. 2008:CD006315.
Hahn et al., Remote ischemic per-conditioning: A novel therapy for acute stroke? Stroke. Aug. 2011;42:2960-2962.
Harkin et al., Ischemic preconditioning before lower limb ischemia-reperfusion protects against acute lung injury. J Vasc Surg. Jun. 2002;35(6):1264-73.
Hoda et al., Remote ischemic perconditioning is effective alone and in combination with intravenous tissue-type plasminogen activator in murine model of embolic stroke. Stroke. Oct. 2012;43(10):2794-9. Epub Aug. 21, 2012.
Hong et al., The effect of remote ischaemic preconditioning on myocardial injury in patients undergoing off-pump coronary artery bypass graft surgery. Anaesth Intensive Care. Sep. 2010;38(5):924-9.
Hopper et al., Role and mechanism of PKC in ischemic preconditioning of pig skeletal muscle against infarction. Am J Physiol Regul Integr Comp Physiol. Aug. 2000;279(2):R666-76.
Jensen et al., Remote ischemic preconditioning protects the brain against injury after hypothermic circulatory arrest. Circulation. Feb. 22, 2011;123(7):714-721. Epub Feb. 7, 2011.

Kanoria et al., Remote ischaemic preconditioning of the hind limb reduces experimental liver warm ischaemia-reperfusion injury. Br J Surg. Jun. 2006;93(6):762-8.
Karuppasamy et al., Remote intermittent ischemia before coronary artery bypass graft surgery: a strategy to reduce injury and inflammation? Basic Res Cardiol. Jun. 2011;106(4):511-9. Epub May 5, 2011.
Kharbanda et al., Translation of remote ischaemic preconditioning into clinical practice. Lancet. Oct. 31, 2009;374(9700):1557-65.
Koch et al., . Remote ischemic limb preconditioning after subarachnoid hemorrhage: a phase Ib study of safety and feasibility. Stroke. May 2011;42(5):1387-91. Epub Mar. 17, 2011.
Kolh Remote ischaemic pre-conditioning in cardiac surgery: benefit or not? Eur Heart J. Jan. 2014;35(3):141-3. doi: 10.1093/eurheartj/eht517. Epub Jan. 6, 2014.
Kottenberg et al., Protection by remote ischemic preconditioning during coronary artery bypass graft surgery with isoflurane but not propofol—a clinical trial. Acta Anaesthesiol Scand. Jan. 2012;56(1):30-8.
Lazaris et al., Protective effect of remote ischemic preconditioning in renal ischemia/reperfusion injury, in a model of thoracoabdominal aorta approach. J. Surg Res. 2009;154:267-273.
Loukogeorgakis et al., Transient limb ischemia induces remote preconditioning and remote postconditioning in humans by a K(ATP)-channel dependent mechanism. Circulation. Sep. 18, 2007;116(12):1386-95. Epub Aug. 27, 2007.
Meng et al., Upper limb ischemic preconditioning prevents recurrent stroke in intracranial arterial stenosis. Neurology. Oct. 30, 2012;79(18):1853-1861. Epub Oct. 3, 2012.
Moretti et al., The EUROpean and Chinese cardiac and renal Remote Ischemic Preconditioning Study (EURO-CRIPS): study design and methods. J Cardiovasc Med (Hagerstown). May 22, 2014. [Epub ahead of print].
Munk et al., Remote ischemic conditioning in patients with myocardial infarction treated with primary angioplasty: impact on left ventricular function assessed by comprehensive echocardiography and gated single-photon emission CT. Circ Cardiovasc Imaging. Nov. 2010;3(6):656-62. Epub Sep. 8, 2010.
O'Riordan, Remote ischemic conditioning increases myocardial salvage during acute MI. Heartwire. Feb. 26, 2010; http://www.theheart.org/article/1050605.do, 1 page.
Pang et al., Acute ischaemic preconditioning protects against skeletal muscle infarction in the pig. Cardiovasc Res. Jun. 1995;29(6):782-8.
Pang et al., Effector mechanism of adenosine in acute ischemic preconditioning of skeletal muscle against infarction. Am J Physiol. Sep. 1997;273(3 Pt 2):R887-95.
Prunier et al., The RIPOST-MI study, assessing remote ischemic perconditioning alone or in combination with local ischemic postconditioning in ST-segment elevation myocardial infarction. Basic Res Cordial. Mar. 2014;109(2):400. doi: 10.1007/s00395-013-0400-y. Epub Jan. 10, 2014.
Rahman et al., Remote ischemic preconditioning in human coronary artery bypass surgery: from promise to disappointment? Circulation. 2010;122:S53-59.
Redington et al., Exploring remote ischaemic preconditioning. Internal Innovation: 42-44. www.research.media.eu.
Ren et al., Limb remote-preconditioning protects against focal ischemia in rats and contradicts the dogma of therapeutic time windows for preconditioning. Neuroscience. Feb. 19, 2008;151(4):1099-103. Epub Dec. 15, 2007.
Rentoukas et al., Cardioprotective role of remote ischemic periconditioning in primary percutaneous coronary intervention: enhancement by opioid action, JACC Cardiovasc Interv. Jan. 2010;(3)(1):49-55.
Saxena et al., Remote ischemic conditioning: evolution of the concept, mechanisms, and clinical application. J Card Surg. Jan.-Feb. 2010;25(1):127-34. Epub Jun. 22, 2009.
Shimizu et al., Effects of intermittent lower limb ischaemia on coronary blood flow and coronary resistance in pigs. Acta Physiol (Oxf). Jun. 2007;190(2):103-9. Epub Mar. 30, 2007.
Shimizu et al., Remote ischemic preconditioning decreases adhesion and selectively modifies functional responses of human neutrophils. J Surg Res. Jan. 2010;158(1):155-61.

(56) References Cited

OTHER PUBLICATIONS

Shimizu et al., Transient limb ischaemia remotely preconditions through a humoral mechanism acting directly on the myocardium: evidence suggesting cross-species protection. Clin Sci (Lond). Aug. 3, 2009;117(5):191-200.
Sloth et al., Improved long-term clinical outcomes in patients with ST-elevation myocardial infarction undergoing remote ischaemic conditioning as an adjunct to primary percutaneous coronary intervention. Eur Heart J. Jan. 2014;35(3):168-75. doi: 10.1093/eurheartj/eht369. Epub Sep. 12, 2013.
Sloth et al., Remote ischemic perconditioning improves long-term clinical outcome in patients undergoing primary percutaneous coronary intervention for ST-Elevation myocardial infarction. J Amer Coll Cardiol. Oct. 23, 2012;60(17):B20. Abstract TCT-63.
Steensrud et al., Pretreatment with the nitric oxide donor SNAP or nerve transection blocks humoral preconditioning by remote limb ischemia or intra-arterial adenosine. Am J Physiol Heart Circ Physiol. 2010. 24 pages.
Takano et al., Late preconditioning enhances recovery of myocardial function after infarction in conscious rabbits. Am J Physiol Heart Circ Physiol. Nov. 2000;279(5):H2372-81.
Thielmann et al., Remote ischemic preconditioning reduces myocardial injury after coronary artery bypass surgery with crystalloid cardioplegic arrest. Basic Res Cardiol. Sep. 2010;105(5):657-64. Epub May 21, 2010.
Thuny et al., Post-conditioning reduces infarct size and edema in patients with ST-segment elevation myocardial infarction. J Am Coll Cardiol. Jun. 12, 2012;59(24):2175-81.
Venugopal et al., Remote ischaemic preconditioning reduces myocardial injury in patients undergoing cardiac surgery with cold-blood cardioplegia: a randomised controlled trial. Heart. Oct. 2009;95(19):1567-71. Epub Jun. 8, 2009.
Venugopal et al., Effect of remote ischemic preconditioning on acute kidney injury in nondiabetic patients undergoing coronary artery bypass graft surgery: a secondary analysis of 2 small randomized trials. Am J Kidney Dis. Dec. 2010; 5(6): 1043-9.
Wagner et al., Myocardial injury is decreased by late remote ischaemic preconditioning and aggravated by tramadol in patients undergoing cardiac surgery: a randomised controlled trial. Interact Cardiovasc Thorac Surg. Dec. 2010;11(6):758-62. doi: 10.1510/icvts.2010.243600. Epub Sep. 16, 2010.
Walsh et al., Remote ischemic preconditioning for renal and cardiac protection during endovascular aneurysm repair: a randomized controlled trial. J Endovasc Ther. Dec. 2009;16(6):680-9.
Wei et al., Repeated remote ischemic postconditioning protects against adverse left ventricular remodeling and improves survival in a rat model of myocardial infarction. Circ Res. May 13, 2011;108(10):1220-5. Epub Apr. 7, 2011. Supplemental Information Included.
Xie et al., Remote ischaemic preconditioning reduces myocardial injury in patients undergoing heart valve surgery: randomised controlled trial. Heart. Mar. 2012;98(5):384-8. Epub Nov. 22, 2011.
Xin et al., Combined local ischemic postconditioning and remote perconditioning recapitulate cardioprotective effects of local ischemic preconditioning. Am J Physiol Heart Circ Physiol, Jun. 2010;298(6):H1819-31. Epub Mar. 5, 2010. Erratum in: Am J PhysiolHeart Circ Physiol. Sep. 2010;299(3):H957.
Zhou et al., Limb ischemic preconditioning reduces heart and lung injury after an open heart operation in infants. Pediatr Cardiol. Jan. 2010;31(1):22-9. Epub Sep. 29, 2009.
Zimmerman et al., Ischemic preconditioning at a remote site prevents acute kidney injury in patients following cardiac surgery. Kidney Int. 2011;80:861-867.
Zografos et al., Remote ischemic preconditioning reduces peri-procedural myocardial injury in elective percutaneous coronary intervention: a meta-analysis. Int J Cardiol. May 15, 2014;173(3):530-2. doi: 10.1016/j.ijcard.2014.03.026. Epub Mar. 15, 2014.
Addison et al., Noninvasive remote ischemic preconditioning for global protection of skeletal muscle against infarction. Am J Physiol Heart Circ Physiol. 2003;285:H1435-1443.
Wang et al., Remote Ischemic Preconditioning Protects against Liver Ischemia-Reperfusion Injury via Heme Oxygenase-1-Induced Autophagy. PLoS One, Jun. 10, 2014;9(6):e98834. doi 10.1371/journal.pone.0098834. eCollection 2014. 12 pages.
Hausenloy et al., Remote ischaemic preconditioning: underlying mechanisms and clinical application. Cardiovasc Res. Aug. 1, 2008;79(3):377-86. doi: 10.1093/cvr/cvn114. Epub May 2, 2008.
Ludman et al., Cardiac preconditioning for ischaemia: lost in translation. Dis Model Mech. Jan.-Feb. 2010;3(1-2):35-8. doi: 10.1242/dmm.003855.
Miki et al., Captopril potentiates the myocardial infarct size-limiting effect of ischemic preconditioning through bradykinin B2 receptor activation. J Am Coll Cardiol. Nov. 15, 1996;28(6):1616-22.
Wang et al., Remote ischemic preconditioning by hindlimb occlusion prevents liver ischemic/reperfusion injury: the role of High Mobility Group-Box 1. Ann Surg. Feb. 2010;251(2):292-9. doi: 10.1097/SLA.0b013e3181bfda8c. Abstract.
Warzecha et al., Ischaemic preconditioning of the hundlimb or kidney does not attenuate the severity of acute ischemia/reperfusion-induced pancreaitis in rats. J Physiol Pharmacol. Jun. 2008;59(2):337-52.
Yellon et al., Preconditioning the myocardium: from cellular physiology to clinical cardiology. Physiol Rev. Oct. 2003;83(4):1113-51.
U.S. Appl. No. 13/021,649, filed Feb. 4, 2011, Andrew Redington.
U.S. Appl. No. 13/542,929, filed Jul. 6, 2012, Caldarone et al.

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial sequence
<220> FEATURE:
<223> OTHER INFORMATION: PCR sense primer for aplpha-MHC

<400> SEQUENCE: 1
ctgctggaga ggttattcct cg                                           22

<210> SEQ ID NO 2
<211> LENGTH: 24
<212> TYPE: DNA
<213> ORGANISM: Artificial sequence
<220> FEATURE:
<223> OTHER INFORMATION: PCR antisense primer for alpha-MHC
```

```
<400> SEQUENCE: 2
ggaagagtga gcggcgcatc aagg                                          24

<210> SEQ ID NO 3
<211> LENGTH: 24
<212> TYPE: DNA
<213> ORGANISM: Artificial sequence
<220> FEATURE:
<223> OTHER INFORMATION: PCR sense primer for beta-MHC

<400> SEQUENCE: 3
tgcaaaggct ccaggtctga gggc                                          24

<210> SEQ ID NO 4
<211> LENGTH: 24
<212> TYPE: DNA
<213> ORGANISM: Artificial sequence
<220> FEATURE:
<223> OTHER INFORMATION: PCR antisense primer for beta-MHC

<400> SEQUENCE: 4
gccaacacca acctgtccaa gttc                                          24

<210> SEQ ID NO 5
<211> LENGTH: 20
<212> TYPE: DNA
<213> ORGANISM: Artificial sequence
<220> FEATURE:
<223> OTHER INFORMATION: PCR sense primer for ANP

<400> SEQUENCE: 5
ctctgagaga cggcagtgct                                               20

<210> SEQ ID NO 6
<211> LENGTH: 20
<212> TYPE: DNA
<213> ORGANISM: Artificial sequence
<220> FEATURE:
<223> OTHER INFORMATION: PCR antisense primer for ANP

<400> SEQUENCE: 6
tatgcagagt gggagaggca                                               20

<210> SEQ ID NO 7
<211> LENGTH: 20
<212> TYPE: DNA
<213> ORGANISM: Artificial sequence
<220> FEATURE:
<223> OTHER INFORMATION: PCR sense primer for beta-tubulin

<400> SEQUENCE: 7
tcactgtgcc tgaacttacc                                               20

<210> SEQ ID NO 8
<211> LENGTH: 20
<212> TYPE: DNA
<213> ORGANISM: Artificial sequence
<220> FEATURE:
<223> OTHER INFORMATION: PCR antisense primer for beta-tubulin

<400> SEQUENCE: 8
ggaacatagc cgtaaactgc                                               20
```

USE OF REMOTE ISCHEMIC CONDITIONING TO IMPROVE OUTCOME AFTER MYOCARDIAL INFARCTION

RELATED APPLICATIONS

This application is a divisional of U.S. Ser. No. 13/021,649 filed Feb. 4, 2011, which claims the benefit of U.S. Provisional Application Ser. No. 61/319,597, filed on Mar. 31, 2010, entitled "USE OF REMOTE ISCHEMIC CONDITIONING TO REDUCE HEART DYSFUNCTION AND/OR HEART FAILURE AFTER MYOCARDIAL INFARCTION", the entire contents of which are incorporated by reference herein.

BACKGROUND OF THE INVENTION

Survivors of myocardial infarction (MI) are at significant risk of heart dysfunction/failure resulting from myocardial remodeling resulting from the MI. This remodeling is associated with poor long-term prognosis, with patients with post-MI congestive heart failure reportedly at a 10-fold higher risk of death as shown in a 5 year follow up study. Treatment of myocardial infarction has concentrated on reducing the period of ischemia and minimizing injury that occurs during post-ischemic reperfusion. Thus, many therapies have aimed to reduce the size of the heart infarct as much as possible or to prevent its occurrence altogether. Recently, deliberate and transient ischemic pre-conditioning has been proposed in order to reduce the effects of ischemic heart injury such as occurs with MI. It has been postulated that this pre-conditioning may essentially induce tolerance in the heart tissue to a later ischemic event such as MI, by reducing the infarct size and thus resulting in a better prognosis.

SUMMARY OF THE INVENTION

The invention relates generally to the use of remote ischemic conditioning (RIC) to reduce the occurrence and/or severity and/or delay the onset of heart dysfunction/failure associated with MI. The invention contemplates the use of RIC on a subject that is experiencing or has experienced an MI. RIC may be performed before and/or during and/or after and MI provided that at least one RIC (including the only RIC) is performed during or after the MI. The invention further contemplates that, in some instances, the subject will undergo more than one RIC regimen. In some important embodiments, the invention contemplates performing RIC on a subject during, or after, or during and after an MI. The RIC is performed repeatedly, in some embodiments, including at least once during the MI and daily, every other day (i.e., every second day), every third day, or every fourth day thereafter for at least 10 days, at least 20 days, at least 28 days, at least 30 days, or longer.

Thus, in one aspect, the invention provides a method comprising performing a repeated RIC regimen on a subject during and/or after an MI. The method may be a method for improving the overall outcome of a subject following MI, including but not limited to reducing the risk of heart dysfunction/failure following an MI, reducing the incidence, frequency and/or severity of the symptoms associated with heart dysfunction/failure following an MI, and/or delaying the onset of heart dysfunction/failure or its associated symptoms, including but not limited to exercise limitation, arrhythmia, and sudden unexpected death following MI. These methods comprise, in another aspect, performing a repeated RIC regimen on a subject having an MI, wherein a first RIC regimen is performed during and/or after (including shortly after) the MI and one or more subsequent RIC regimens are performed at least every 7, every 6, every 5, every 4, every 3, or every 2 days, or every day after the first RIC regimen.

In one aspect, the invention provides a method comprising performing a repeated RIC regimen on a subject having an MI, wherein a first RIC regimen is performed during the MI and subsequent RIC regimens are performed daily after the first RIC regimen.

In one aspect, the invention provides a method comprising performing a repeated RIC regimen on a subject that has experienced an MI. In one embodiment, the subject has been given an RIC regimen during the MI or within 36 hours, within 24 hours, within 12 hours, within 6 hours, within 3 hours, within 2 hours, or within 1 hour of the MI, optionally locally or remotely.

In one aspect, the invention provides a method comprising performing repeated RIC regimens on a subject after an MI. In some embodiments, the repeated RIC regimens are commenced within 1 week or within 1 month of the MI. In some embodiments, the subject has not undergone prior ischemic conditioning during the MI.

In some embodiments, the subject has not undergone ischemic conditioning prior to the MI. In some embodiments, the subject has undergone ischemic conditioning prior to the MI. In some embodiments, the ischemic conditioning prior to the MI was local or remote. In some embodiments, the ischemic conditioning during the MI was local or remote. It is to be understood that as used herein ischemic conditioning is a deliberate regimen performed on a subject and it does not embrace the ischemic and reperfusion phases that "naturally" occur during an MI.

In some embodiments, the method does not impact (e.g., reduce) the size of the infarct that results from the MI (i.e., the infarct size remains relatively unchanged by the method).

In some embodiments, the first RIC regimen is performed during ischemia associated with MI. In some embodiments, the first remote ischemic conditioning regimen is performed during reperfusion following ischemia associated with MI. In some embodiments, the first RIC regimen is performed during the ischemia associated with MI only, or during the ischemia performed during the ischemia associated with MI and then every day thereafter, every two days thereafter, every three days thereafter, every four days thereafter, every five days thereafter, every six days thereafter, or every seven days thereafter.

In some embodiments, the subsequent RIC regimens are performed every three days, every two days, or every day after the first RIC regimen or after the MI.

In some embodiments, the subsequent RIC regimens are performed for one or more months after the MI. In some embodiments, the repeated RIC regimens comprise more than one (e.g., 2, 3, 4, 5 or more) RIC regimens per day on one or more days.

In preferred embodiments, the subject is human. In some embodiments, the subject is not at risk of restenosis, as described in greater detail herein. In some embodiments, the subject does not have a chronic medical condition such as hypertension.

The number of cycles per RIC regimen may be two, three, four, five, six or more cycles, with each cycle comprising supra-systolic pressure and reperfusion. In some embodiments, at least one RIC regimen of the repeated RIC regimen comprises at least four cycles. In some embodiments, at least one RIC regimen of the repeated RIC regimen comprises more than one cycle comprising 5 minutes of supra-systolic pressure and 5 minutes of reperfusion. In some embodiments, the supra-systolic pressure is a pressure that is at least an absolute number of mmHg above systolic pressure, or it is a percentage above of systolic pressure. The supra-systolic pressure may be a pressure that is 5, 10, 15, 20, 25, 30, 35, 40, 45, 50 or more mmHg above systolic pressure. In some embodiments, the supra-systolic pressure is a pressure that is at least 15 mmHg above systolic pressure, and may range to 20, 25, 30, 35, 40, 45, 50 or more mmHg above systolic pressure. In some embodiments, the supra-systolic pressure is a pressure that is 1%, 2%, 3%, 4%, 5%, 6%, 7%, 8%, 9%, 10% or more than systolic pressure. It is to be understood that these percentages reflect a percentage of the systolic pressure, such that the supra-systolic pressure may also be referred to as being at a level that is 101%, 102%, 103%, 104%, 105%, 106%, 107%, 108%, 109%, 110% (or more) of systolic pressure. In some embodiments, the supra-systolic pressure is at or about an absolute pressure such as for example at or about 170, 180, 190, 200, 210, 220, 230 or more mmHg. In some embodiments, the supra-systolic pressure is a pressure that is at or about 200 mmHg.

In some embodiments, each of the RIC regimens in the repeated RIC regimen is performed at the same site. In some embodiments, the repeated RIC regimen is performed on an upper limb. In one embodiment, an individual RIC regimen or a repeated RIC regimen is performed using two or more devices such as two or more cuffs, positioned at different sites on the body (e.g., one cuff per arm, or one cuff per leg, or one cuff on an arm and one cuff on a leg, etc.).

In some embodiments of the foregoing aspects, the subject is further treated using a defibrillator. The defibrillator may be an automated external defibrillator (AED).

In some embodiments, the method further comprises administering to the subject an angiotensin-converting enzyme (ACE) inhibitor. Examples of ACE inhibitors suitable to the invention include but are not limited to captopril, enalapril, ramipril, lisinopril, quinapril, fosinopril, benazepril, and moexipril.

In some embodiments, the method further comprises administering to the subject an angiotensin II receptor blocker. Examples include but are not limited to candesartan, irbesartin, losartin, telmisartin, and valsartan.

In some embodiments, the method further comprises administering to the subject an anti-platelet agent. Examples include aspirin and clopidogrel.

In some embodiments, the method further comprises administering to the subject a statin.

In various embodiments, the subject may be administered two or more of these aforementioned agents.

In another aspect, the invention provides a kit comprising a defibrillator and a device for performing remote ischemic conditioning, such as for example the automated device described herein. The defibrillator may be an automated external defibrillator (AED).

These and other aspects and embodiments of the invention will be discussed in greater detail herein.

BRIEF DESCRIPTION OF THE FIGURES

The accompanying figures are not intended to be drawn to scale. In the figures, each identical or nearly identical component that is illustrated in various figures is represented by a like numeral. For purposes of clarity, not every component may be labeled in every figure.

Various embodiments of the invention will now be described, by way of example, with reference to the accompanying figures, in which.

Figure 1:
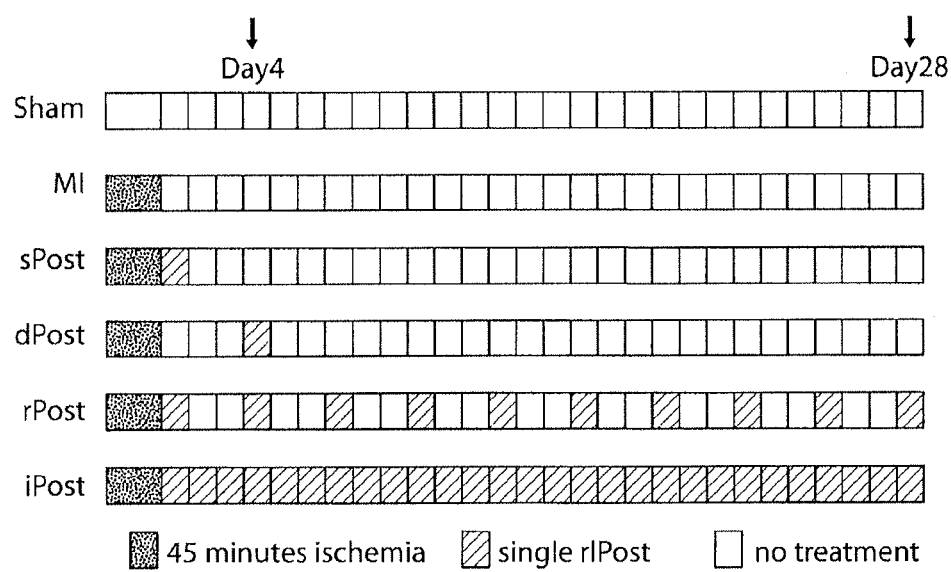
FIG. 1 is a schematic figure illustrating the experimental protocol, in which rats were randomly assigned to different groups: 1) Sham group, where rats underwent sham operation without any intervention; 2) MI group, rats underwent 45 minutes ischemia followed by reperfusion with no conditioning therapy given; 3) sPost group, a single conditioning event was delivered before the end of ischemia and continued during the initial reperfusion period; 4) dPost group, a single conditioning event was delivered on day 4 (72 hours after reperfusion); 5) rPost group, conditioning was given as in group 3 and then given every three days until day 28 and 6) iPost group, conditioning was given as in group 3 and then given every day until day 28, in which vertical arrows indicate the dates (day 4 and day 28, respectively) for euthanization, and in which all the abbreviations are the same as in the text.

Table 1 presents data obtained from each group of rats to assess cardiac geometry, function, infarct size and hemodynamic changes.

DETAILED DESCRIPTION OF THE INVENTION

The invention is premised, in part, on the finding that heart dysfunction/failure post-MI can be reduced, delayed or prevented altogether by deliberately and, in some instances, repeatedly performing cycles of induced transient ischemia and reperfusion in subjects during and/or after an MI. The invention is also premised in part on the finding that performing induced transient ischemia and reperfusion on subjects during an MI, including during the ischemia associated with an MI has similar benefits. The use of induced transient ischemia and reperfusion according to the invention is also associated with increased survival in subjects post-MI.

The invention provides methods for reducing the risk, delaying the onset, and/or reducing the severity of heart dysfunction/failure following MI. The invention aims to ameliorate or prevent heart dysfunction/failure that occurs as a result of MI. The invention does so by subjecting the subject having or who has had an MI to one or more RIC regimens. In some aspects of the invention, at least one of these regimens (including the only one that the subject may receive) is performed during the MI. These are referred to as "per-conditioning" regimens, and they can occur during the ischemic phase of an MI and/or the reperfusion phase that follows. In certain embodiments, subjects receive an RIC regimen during the MI, including during the ischemic phase of the MI. In these and other aspects of the invention, one or more regimens may be performed following the MI. These are referred to as "post-conditioning" regimens. Thus, some methods of the invention involve performing RIC on a subject while such subject is experiencing an MI, and optionally after the MI. Other methods of the invention involve performing RIC on a subject following an MI, optionally if an RIC regimen has been performed on the subject during the prior MI. In some embodiments, RIC may be performed during an MI (e.g., during the ischemic phase of an MI, during the reperfusion phase of an MI, or during the ischemic and reperfusion phases of the MI), and/or immediately after the cessation of an MI (e.g., within hours, and preferably within an hour), and/or following the MI (as discussed below). In some embodiments, the subject has not received any pre-conditioning RIC regimens (i.e., an RIC regimen before the MI). In some embodiments, the subject has received one or more pre-conditioning RIC regimens.

Thus, in some aspects, the methods involve performing RIC during the MI and repeatedly after the MI. In some aspects, the methods involve performing RIC repeatedly after an MI even if RIC was not performed during the MI. Such RIC may be referred to herein as post-MI RIC. In some embodiments, post-MI RIC is performed days, weeks, or months after an MI. Thus the time in between the MI and the first RIC may be 1, 2, 3, 4, 5, or 6 days, or 1, 2, 3, or 4 weeks, or 1, 2, 3, 4, 5, 6, or more months, or longer.

In some embodiments, heart function is improved and/or heart dysfunction/failure is reduced, as described above, even if the infarct itself is not affected by the RIC that occurs post-MI. That is, the infarct size does not appear to be impacted by the post-MI RIC relative to the effect of a single RIC at the time of the MI. In some embodiments, survival time is increased.

It has been found quite surprisingly, according to the invention, that subjecting an individual to RIC during and after MI protects the subject against adverse remodeling that otherwise occurs following ischemic and reperfusion heart injury, such as most typically occurs with an MI. Even more surprisingly, this benefit is achieved even if there is no effect on infarct size. That is, the long term remodeling effects do not appear to be associated with any change (e.g., reduction) in infarct size resulting from the MI.

It is also surprising that the post-conditioning regimens have been found to provide therapeutic benefit particularly since it had been thought heretofore that ischemic conditioning had to be performed prior to an ischemic event (i.e., "pre-conditioning"). The invention evidences that, regardless of whether a subject has undergone any form of ischemic pre-conditioning, it can still benefit from ischemic post-conditioning at least to the extent that such post-conditioning reduces or prevents heart dysfunction/failure associated with MI.

As described in the Examples, therapeutic post-MI benefit can be achieved by performing a single RIC regimen on a subject during an MI. This regimen may occur during the ischemic phase of an MI and/or during the reperfusion phase of an MI. Thus, the invention contemplates, in some instances, that once a subject is identified as one having an MI, as known in the art and as described below, then someone attending to that subject, including but not limited to medically trained personnel, will perform an RIC regimen on that subject. This regimen, as described in greater detail below, involves performing one and preferably more than one ischemia-reperfusion cycle to a remote location on the subject. Such locations are preferably easily accessible and the regimen is preferably a non-invasive regimen. Typically, the regimen is performed on one or more limbs through application of pressure at the skin (for example, through the use of a pressure cuff or a tourniquet).

In the experimental model used in the Examples, a single conditioning regimen during the reperfusion phase of an MI provided long-term benefit while a single conditioning regimen performed at day 4 (with the MI beginning on day 1) had no effect.

Thus, in some embodiments of the invention, an RIC regimen is performed within 30 days, or within 20 days, 10 days or within one 1 day, or within 12 hours, or within 6 hours, or within 3 hours, or within 2 hours, within 1 hour, within 30 minutes, within 10 minutes, or within 5 minutes of the myocardial infarction, and/or at the time of the myocardial infarction.

The Examples further show, again surprisingly, that even more benefit can be obtained when multiple RIC regimens are performed on the subject post-MI. More specifically, more protection against the adverse effects of remodeling and increased survival time were observed when multiple RIC regimens were performed following the MI. It was found that performing RIC once every three days after the MI provided greater protection than a single regimen at the time of the MI. Importantly, infarct size was not significantly different between the two groups of animals, indicating that the beneficial effects provided by this early conditioning regimen were independent of effect on the infarct.

It was further found that performing RIC daily after the MI provided even greater protection and higher rates of survival than when it was performed once every three days.

Accordingly, the invention in some instances provides methods that involve performing RIC on a subject at least once a week, at least once every 6 days, at least once every 5 days, or at least once every 4 days following an MI, preferably where RIC has also been performed during the MI. In some important embodiments, the remote ischemic conditioning is performed on a subject at least once every 3 days, at least once every 2 days, or at least once every day (i.e., daily) following an MI, preferably where RIC has also been performed during the MI.

As used herein, "at least once" as in for example "at least once every three days" means that in a three day period at least one RIC regimen is performed. As a result, this includes instances in which the RIC is performed every day, every two days, or every three days. Alternatively or additionally it includes instances in which on the first, second, and/or third day of the three day period, one or more RIC regimens are performed. In the simplest case, one RIC is performed every three days. However, it is to be understood that the invention contemplates more frequent performance on any given day. It is also to be understood that this same meaning applies for regimens that are performed at other frequencies, as recited above. Thus, for the sake of clarity, "at least daily" means that every day one or more RIC regimens is performed.

In some embodiments, a single RIC regimen is performed on a single day. In other embodiments, more than one, including 2, 3, 4, 5 or more, RIC regimens are performed on a single day.

Whether performed on a single day or on different days, the RIC regimen may be performed at the same location or at different locations. These may alternate between two locations or they may cycle through more than two locations. The use of more than one location may be determined a priori or it may be random. In some embodiments, a single regimen may be performed using a single location or multiple locations. For example, a single regimen may be performed at a single location on an upper arm of a human subject or it may be performed using two upper arm locations (e.g., separate upper arms) simultaneously or in an alternating manner. When multiple locations are used, two or more devices may be used.

The foregoing regimens are considered to be regular in nature to the extent that the frequency of the regimens is determined a priori and carried out in like manner. It will be clear that the time in between regimens may be uniform (or identical) or it may differ, provided that such timing is known ahead of time. The invention contemplates protocols in which at least two sets of two contiguous regimens are separated by a first time period and at least two other sets of two contiguous regimens are separated by a second time period that is different from the first time period.

The invention however contemplates the performance of randomly spaced multiple regimens post-MI, provided however that even in such instances the regimens are performed at least as frequently as once every week.

The remote ischemic conditioning regimens may be performed over any time period including without limitation for up to 1 month, 2, 3, 4, 5, 6, 7, 8, 9, 10, 11, or 12 months, or longer following an MI. In some instances, the regimens occur over years including up to 2, 3, 4, 5, or more years. In still other instances, the regimens continue over the remaining lifespan of the subject or until it is determined that the subject is no longer at an elevated risk of heart dysfunction/failure. As used herein, an elevated risk of heart dysfunction/failure is a risk that is higher than the risk of the average population that has not experienced an MI. Thus, although the Examples show the effects of RIC regimens that are performed up to 30 days post-experimentally simulated MI, the invention contemplates both shorter and longer "treatment" times.

The subjects to be "treated" by the invention minimally are experiencing or have experienced an MI. They may or may not have been subjected to ischemic pre-conditioning (i.e., ischemic conditioning prior to the MI). They may or may not have a condition for which ischemic conditioning, including ischemic pre-conditioning, is indicated. They may or may not be at risk of restenosis, for example following a medical procedure or intervention that involves widening or dilation of a blood or other vessel in the body. Examples of such medical procedures or interventions include but are not limited to angioplasty or stent placement. Similarly, the subject may or may not be one who has undergone a medical intervention that induced or is likely to induce vessel damage. The subject may or may not present with or have a history of a chronic medical condition such as but not limited to hypertension. The subjects of the invention will preferably be humans, although non-human subjects are also contemplated.

As used herein, the term "treat" means to have a positive or therapeutic benefit on the likelihood, onset time, and/or severity of heart dysfunction/failure the subject may experience post-MI. Such positive or therapeutically beneficial effects may be measured by comparing the subject to a population that has not been subjected to the methods of the invention. The subject and the population can be compared in terms of incidence of heart dysfunction/failure, time of onset of heart dysfunction/failure, and severity of heart dysfunction/failure. Heart dysfunction/failure indicia are described in greater detail below.

Based on the foregoing, therefore, it should be clear that the invention contemplates performing RIC regimens on subjects who are having an MI as well as those who have already had an MI particularly if these latter subjects were administered an ischemic conditioning regimen at or near the time of the MI, whether locally or remotely.

Those of ordinary skill in the art, including but not limited to medical practitioners and medical emergency personnel, will be familiar with the characteristics of an MI. Symptoms of MI, particularly in men, include sudden chest pain (often times radiating to the left arm or left side of neck), shortness of breath, nausea, vomiting, palpitations, sweating, and anxiety. Symptoms in women differ somewhat from those in men, and typically include shortness of breath, weakness, indigestion, and fatigue. Whether in the presence or absence of such symptoms, MI may be detected using, for example, electrocardiograms, blood marker tests (e.g., creatine-kinase, troponin T or I), and heart imaging such as chest X-rays. Guidelines for diagnosing an MI include the WHO criteria (i.e., history of ischemic type chest pain lasting for more than 20 minutes, changes in serial ECG tracings, and rise/fall of serum cardiac markers such as creatine kinase MB and troponin) in which the presence of two and three such criteria indicate probable and definite MI, respectively.

As used herein, the term "remote ischemic conditioning regimen" or "RIC regimen" refers to one or more ischemia-reperfusion cycles performed on a subject at a location on the body other than the heart (i.e., a "remote" location). As used herein, an RIC regimen (or an individual RIC regimen) means at least one cycle of an induced transient ischemic event followed by a reperfusion event. An individual RIC regimen therefore may be comprised of 1, 2, 3, 4, 5, or more such cycles.

The invention contemplates, in some aspects, performing a repeated RIC regimen on a subject. As used herein, a repeated RIC regimen is two or more individual RIC regimens that occur on a single day and/or one or more RIC regimens that occur on a number of days. For example, the repeated RIC regimen may comprise performing multiple RIC regimens on a single day, or performing single RIC regimens on a number of days, or performing multiple RIC regimens on a number of days. If the repeated RIC regimen occurs on a single day, the time between individual regimens may be at least 10 minutes, at least 20 minutes, at least 40 minutes, at least 1 hour, at least 2 hours, or at least 6 hours, for example. If the repeated RIC regimen occurs over the course of several days, the time between individual regimens may be 1 day, 2 days, 3 days, 4 days, 5 days, 6 days or 7 days. The totality of the repeated RIC regimens is referred to herein as an RIC protocol.

As discussed herein, there is no requirement that any or all of the RIC regimens in a repeated RIC regimen be identical with respect to timing, number of cycles per regimen, supra-systolic pressure, location, and the like.

Typically, RIC is performed on a limb such as an upper or lower limb, although it is not so limited. The repeated RIC regimen may be performed on a single site or on multiple sites in the body. For example, the repeated RIC regimen may comprise a first RIC regimen performed on the right upper arm, followed by a second RIC regimen performed on the left upper arm. The repeated RIC regimen may comprise alternation between remote sites on the body. In some instances, an RIC regimen may be performed on a subject at two different sites at overlapping times including simultaneously. In such instances, two devices may be used, as described below.

Heart Dysfunction/Failure

Heart failure is defined as the inability of the heart to pump blood through the body or to prevent blood from backing up into the lungs. Heart failure is often times referred to as congestive heart failure and is associated with systolic or diastolic heart dysfunction. It typically develops over time and may be triggered or exacerbated by another condition that causes heart tissue damage (e.g., an MI) or that causes the heart tissue to work more (or harder) than normal.

Accordingly, and as will be understood by those of ordinary skill in the art, heart failure indicates heart dysfunction and the invention contemplates reducing the risk, delaying the onset, preventing and/or treating heart dysfunction in the presence or absence of heart failure. The discussion of heart failure herein is therefore intended to capture heart dysfunction also, unless stated otherwise.

The invention provides, in some instances, methods for reducing the risk of heart dysfunction/failure in subjects who have had or are having an MI. The method is intended to reduce the development and/or severity of heart dysfunction/failure and its associated symptoms which include but are not limited to, exercise intolerance, arrhythmia and sudden death, as a result of the MI. Development and severity of heart dysfunction/failure can be measured by monitoring and measuring symptoms or other characteristics associated with heart dysfunction/failure. These are discussed below. The methods may lead to the prevention of all or some such symptoms, the delayed onset of all or some such symptoms, and/or the reduction in the severity of all or some such symptoms. A reduction in the risk of heart dysfunction/failure may be determined by monitoring the symptoms or other characteristics associated with heart dysfunction/failure in the treated subject and comparing the number, onset, and severity of such symptoms or characteristics in that subject with historical population data for heart dysfunction/failure. For example, it is known that subjects that survive MI are more likely to develop heart dysfunction/failure than the average population. The methods of the invention aim to reduce this likelihood or risk of heart dysfunction/failure development.

Symptoms of heart dysfunction/failure include shortness of breath (dyspnea), swelling in the feet and legs (edema) typically as a result of abnormal fluid retention, fluid in the lungs, persistent coughing or wheezing, low exercise tolerance, general fatigue even in the absence of exercise, increased heart rate (or palpitations), loss of appetite, memory loss (or confusion), and nausea. One and typically more than one of these symptoms will be manifest in subjects having heart dysfunction/failure. The methods of the invention aim to prevent the development, delay the onset, and/or reduce the severity of one or more of these symptoms.

Heart dysfunction/failure can be diagnosed based on presentation of one and typically more than one of the foregoing symptoms. Heart dysfunction/failure can also be diagnosed or a suspected diagnosis of heart dysfunction/failure can be confirmed with tests such as an electrocardiogram (ECG or EKG), an echocardiogram ("cardiac echo"), or cardiac catheterization. Echocardiograms, for example, are able to measure the volume or fraction of blood that is ejected from the left ventricle with each beat. This is referred to as the ejection fraction. In normal subjects, about 60% of the blood in the left ventricle is ejected. Subjects may present with mildly depressed ejection fractions (e.g., 40-45%), moderately depressed ejection fractions (e.g., 30-40%), or severely depressed ejection fractions (e.g., 10-25%). Thus, in some aspects of the invention, the methods aim to maintain the ejection fraction, particularly if the subject presents with normal or mildly depressed ejection fractions. In some aspects, the methods of the invention aim to delay the onset of a depressed ejection fraction, regardless of the initial ejection fraction presentation. Stress tests may also be used to diagnose heart dysfunction/failure, and they may be combined with one or more of the imaging tests discussed above. For example, a stress test may be combined with an echocardiogram in order to monitor and measure heart dysfunction/failure before, during and/or following exercise periods. Those of ordinary skill in the art, including medical practitioners and more particularly cardiologists, will be familiar these tests and their use in diagnosing heart dysfunction/failure.

It will be understood that the subjects intended to be treated according to the methods of the invention will also have a history of or evidence for, one or more MI. In some aspects, the subject may or may not present or have a history of other risk factors or other conditions. For example, in one embodiment, the subjects may not have a history and/or may not present with high blood pressure (hypertension). As another example, in one embodiment, the subjects may not have undergone a medical procedure or intervention that aims to dilate a tube such as an artery or vein in the subject. Examples of such interventions include angioplasty, stent placement, and the like.

Importantly, in some instances, one or more of the benefits provided by the methods of the invention occur independently of any effect on the myocardial infarct size or volume. That is, as described in the Examples, in some embodiments provided a first cycle of RIC is applied during an MI or shortly thereafter, the infarct size may not be significantly reduced through subsequent chronic RIC. However, surprisingly, even in the absence of any further reduction in the infarct size, it is still possible to reduce the risk, onset and/or severity of heart dysfunction/failure using the methods of the invention. Although not intending to be limited to any particular mechanism of action to explain this finding, chronic RIC may prevent or restrict the degree of left ventricular remodeling that occurs post-myocardial infarction. As discussed in the Examples, repeated post-MI RIC regimens may attenuate inflammatory responses, reduce oxidative stress, and/or modulate hypertrophic and fibrotic signals associated with MI.

Some methods of the invention therefore comprise performing an RIC regimen on a subject during and/or after (including shortly after) a myocardial infarction. Preferably, one RIC regimen is performed on the subject during the myocardial infarction. In these embodiments, it may be performed during the ischemic phase (or period), or during the reperfusion phase (or period), or it may overlap both phases to varying degrees. If performed during the myocardial infarction, the conditioning is referred to herein as perconditioning. In other embodiments, the RIC regimen is performed within 30 minutes, within 1 hour, 2 hours, 3 hours, 4 hours, 5 hours, 6 hours, 8 hours, 10 hours, 12 hours, 18 hours, or 24 hours of the end of the ischemic period of the myocardial infarction. In still other embodiments, the RIC regimen is performed within 36 hours, 48 hours, or 60 hours of the myocardial infarction.

Subsequent RIC regimens may be performed on a daily basis, every other day, or every three days. These RIC regimens may be performed once a day, or more than once a day, including twice a day, 3 times a day, or more.

Additional Therapies

The RIC regimens of the invention may be used in combination with other therapies or procedures aimed at reducing the risk or severity of heart dysfunction/failure. These therapies include without limitation antiplatelet drug therapy including fibrinolytic agents, anti-coagulation agents, and platelet function inhibitors, beta blocker therapy, ACE inhibitor therapy, statin therapy, aldosterone antagonist therapy (e.g., eplerenone), and omega-3-fatty acids therapy. Depending upon the embodiment, one or more of these agents may be administered before, at the time of, or after MI, whether or not overlapping with the RIC regimens and/or protocol. These and other suitable therapies are discussed in greater detail below.

Fibrinolytic agents are agents that lyse a thrombus (e.g., a blood clot), usually through the dissolution of fibrin by enzymatic action. Examples include but are not limited to ancrod, anistreplase, bisobrin lactate, brinolase, Hageman factor (i.e. factor XII) fragments, molsidomine, plasminogen activators such as streptokinase, tissue plasminogen activators (TPA) and urokinase, and plasmin and plasminogen.

Anti-coagulant agents are agents that inhibit the coagulation pathway by impacting negatively upon the production, deposition, cleavage and/or activation of factors essential in the formation of a blood clot. Anti-coagulant agents include but are not limited to vitamin K antagonists such as coumarin and coumarin derivatives (e.g., warfarin sodium); glycosoaminoglycans such as heparins both in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, tinzaparin sodium, inhibitors of factor Xa, factor TFPI, factor VIIa, factor IXc, factor Va, factor VIIIa as well as inhibitors of other coagulation factors.

Inhibitors of platelet function are agents that impair the ability of mature platelets to perform their normal physiological roles (i.e., their normal function). Examples include but are not limited to acadesine, anagrelide, anipamil, argatroban, aspirin, clopidogrel, cyclooxygenase inhibitors such as nonsteroidal anti-inflammatory drugs and the synthetic compound FR-122047, danaparoid sodium, dazoxiben hydrochloride, diadenosine 5',5'''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin ($PGI_2$), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and anti-serotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred anti-inflammatory agent is aspirin.

Lipid reducing agents include gemfibrozil, cholystyramine, colestipol, nicotinic acid, probucol lovastatin, and statins such as fluvastatin, simvastatin, atorvastatin, pravastatin, and cirivastatin.

Direct thrombin inhibitors include hirudin, hirugen, hirulog, agatroban, PPACK, thrombin aptamers.

Glycoprotein IIb/IIIa receptor inhibitors are both antibodies and non-antibodies, and include but are not limited to ReoPro (abcixamab), lamifiban, tirofiban.

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

Beta-adrenergic receptor blocking agents (also known as beta blockers) are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propyl-thio)-4-(5-carbamoyl-2-thienyl)thiazol,7-(2-hydroxy-3-t-butylaminpropoxy)phthalide. The above-identified compounds can be used as isomeric mixtures, or in their respective levorotating or dextrorotating form.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include but are not limited to peptidic compounds (e.g., saralasin, [(San$^{1)}$(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexyl-amide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche A G); $A_2$ agonists (Marion Merrill Dow) and certain non-peptide heterocycles (G. D. Searle and Company).

ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart dysfunction/failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

HMG-CoA reductase inhibitors include, but are not limited to, statins such as simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

It is to be understood that the invention contemplates the use of one or more of any of the foregoing agents in combination with the repeated RIC regimens of the invention.

RIC

As used herein, an RIC regimen is at least one cycle of an induced transient ischemic event followed by a reperfusion event. Typically, these regimens are performed by restricting blood flow in a limb or a peripheral tissue of the subject and then removing the blood flow restriction and allowing blood to reperfuse the limb or tissue. An RIC regimen is typically non-invasive. A regimen may comprise a single cycle or multiple cycles, including 2, 3, 4, 5, or more cycles. In one important embodiment, a regimen comprises 4 cycles of ischemia and reperfusion.

The blood flow restriction typically takes the form of an applied pressure to the limb or tissue that is above systolic pressure (i.e., supra-systolic pressure). It may be about 5, about 10, about 15, about 20, or more mmHg above (or greater than) systolic pressure. Since systolic pressure will differ between subjects, the absolute pressure needed to induce ischemia will vary between subjects. In other embodiments the pressure may be preset at, for example, 200 mmHg. The blood flow restriction may be accomplished using any method as the invention is not limited in this regard. Typically, it may be accomplished with an inflatable cuff, although a tourniquet system is also suitable. Further examples of automated devices for performing RIC are described below.

The induced ischemic event is transient. That is, it may have a duration of about 1, about 2, about 3, about 4, about 5, or more minutes. Similarly, the reperfusion event may have a duration of about 1, about 2, about 3, about 4, about 5, or more minutes. The Examples demonstrate the effect of 4 cycles of 5 minutes of ischemia followed by 5 minutes of reperfusion on physical performance.

If performed using a limb, the upper limb or lower limb may be used although in some instances the upper limb is preferred. In some instances, RIC is performed on two different sites on the body, in an overlapping or simultaneous manner.

RIC may be performed using any device provided it is capable of inducing transient ischemia and reperfusion, whether manually or automatically.

In one of its simplest forms, the method may be carried out using a sphygmomanometer (i.e., the instrument typically used to measure a subject's blood pressure). The cuff of the sphygmomanometer is placed about a subject's limb (e.g., an arm or leg) and is inflated to a pressure great enough to occlude blood flow through the limb (i.e., a pressure greater than the subject's systolic blood pressure). The cuff is maintained in the inflated state to prevent blood flow through the limb for a specified period of time, referred to herein as the ischemic duration. After the ischemic duration, pressure is released from the cuff to allow reperfusion of blood through the limb for a period of time that is referred herein as the reperfusion duration. The cuff is then re-inflated and the procedure is immediately repeated a number of times.

The method may similarly be carried out using a manual type tourniquet. Devices such as those described in published PCT application WO 83/00995 and in published US application 20060058717 may also be used.

Another system that may be used is described in published US application 20080139949. The advantage of this system is that it can be used independently of a medical practitioner, and that it automatically induces the required RIC regimen. This system is exemplified in part in FIG. 8, which illustrates a cuff 10, an actuator 12, a controller 14 and a user interface 16. The cuff is configured to be placed about the limb 15 of a subject, such as an arm or leg of the subject. The actuator, when actuated, causes the cuff to retract about the limb to occlude blood flow through the limb. The controller executes a protocol that comprises repeating a cycle one or more times. The cycle itself includes actuating the cuff to prevent blood flow, maintaining the cuff in an actuated state for an ischemic duration, releasing the cuff, and maintaining the cuff in a relaxed state to allow reperfusion.

Figure 9:
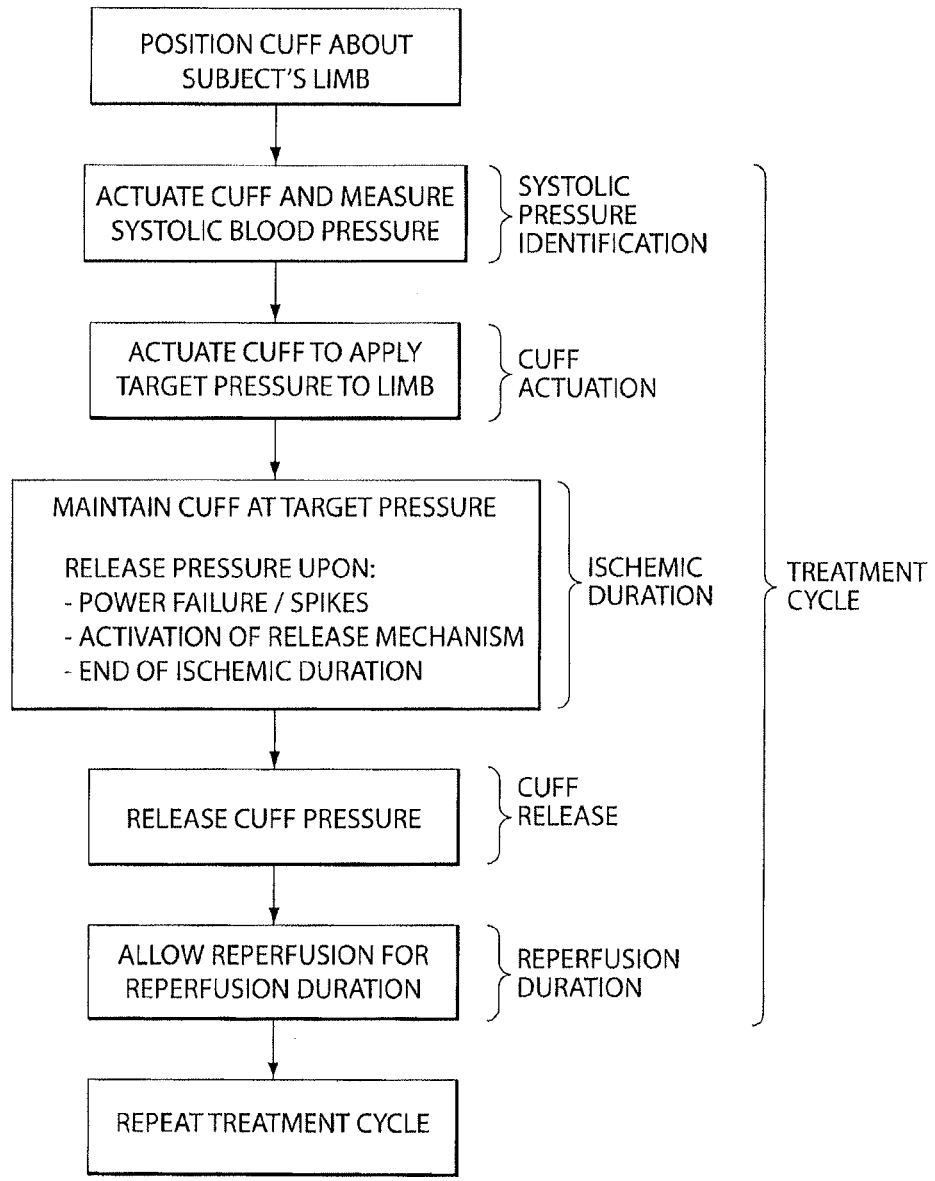
FIG. 9 is a block diagram of one embodiment of an operating scheme of the RIC system.

FIG. 9 shows a block diagram that represents a scheme that may be used to perform RIC. The scheme begins with placement of a cuff about a subject's limb. The system is then activated and the protocol is initiated through the controller. In one embodiment, the system is activated by a medical professional. In another embodiment, the system may be activated by the subject. The cuff contracts to apply an initial pressure, greater than systolic pressure, to the subject's limb. As discussed herein, the initial pressure may be a default value of the system or may be programmed into a particular protocol. The cuff then deflates to identify the subject's systolic pressure. This may be accompanied by monitoring the subject for the onset of Korotkoff sounds or vibrations. Alternatively or additionally, a distal remote sensor (e.g., a device on the fingertip which is sensitive to the presence or absence of flow or maintenance of flow) may be used. Once systolic pressure has been identified, the system initiates the first cycle of the protocol. In some embodiments, systolic pressure may be identified as an initial portion of the protocol. As used herein, the terms protocol and regimen are used interchangeably.

The cycle begins as the cuff contracts to apply a target pressure, greater than the subject's systolic pressure by an amount defined in the protocol, to the subject's limb. This occludes blood flow through the subject's limb. The external pressure against the subject's limb is held for an ischemic duration defined in the protocol. The system monitors the subject during the ischemic duration for pressure release criteria, which may include system power failure, system power spikes, and manual activation of quick release mechanism. The system also monitors the subject during the ischemic duration for any signs of reperfusion through the subject's limb, and accordingly, increases the external pressure applied by the cuff to prevent such reperfusion. Signs of reperfusion can include the onset of Korotkoff sounds or vibrations. After passage of the ischemic duration, the cuff releases pressure from about the subject's limb to allow reperfusion. Reperfusion is allowed for a reperfusion duration defined in the cycle.

The initial cycle typically concludes after the reperfusion duration. At this time, a subsequent cycle may begin as the cuff is actuated to contract about the subject's limb to occlude blood flow through the limb for another ischemic duration.

Figure 8:
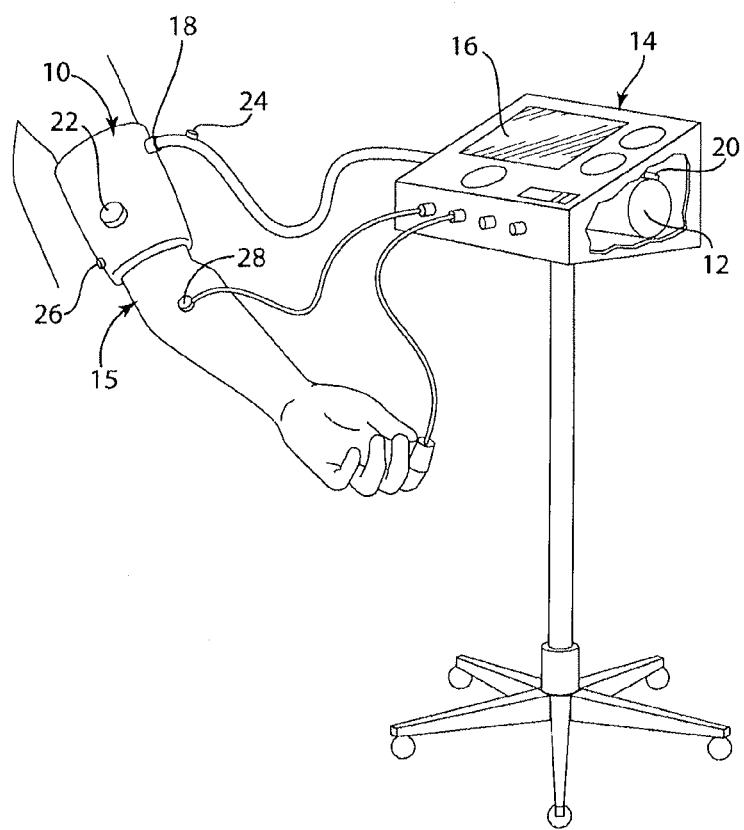
FIG. 8 is a schematic representation of one embodiment of a remote ischemic conditioning system, including a pneumatically inflatable cuff configured to contract about the limb of a subject.

The cuff illustrated in FIG. 8 is configured to be positioned about the limb of a subject and to contract about the limb when actuated. In one embodiment, the sleeve is wrapped about a subject's upper arm, calf, or thigh and is fastened snuggly in place. Portions of the cuff may include hook and loop type material that can be used to fasten the sleeve in place about the subject's limb. The actuator inflates the cuff such that the limb is constricted to the point of occluding blood flow through the subject's limb.

The illustrated cuff includes an inflatable bladder (not shown) that receives a fluid, such as air, to cause the cuff expand and retract about a subject's limb. The bladder is constructed of an air impermeable material, such as flexible plastic or rubber. A connection port 18 is present at one end of the bladder to allow air to enter the bladder during inflation, or to exit the bladder during deflation. The port may include engagement features to facilitate a connection to the actuator, such as by an air hose. These features may include threads, clips, and the like. Although the illustrated embodiment includes a single bladder positioned within a cuff, it is to be appreciated that other embodiments are also possible. By way of example, according to some embodiments, the fabric sleeve may itself be air impermeable, such that no separate bladder is required. In other embodiments, multiple, separate inflatable bladders may be incorporated into a common sleeve, as aspects of the present invention are not limited in this respect.

The general size of subjects that undergo RIC may vary greatly, particularly given the range of species to which the methods may be applied. Given this variance, it may be desirable for some embodiments of cuffs to be adjustable over a wide range to accommodate the variety of subject limb girths that may be expected. According to some embodiments, the cuff comprises an inflatable fabric sleeve having a length greater than three feet, such that a girth of up to three feet may be accommodated. Embodiments of cuffs may include a width as small as two inches, one inch, or even smaller, so as to accommodate the upper arm or leg of a much smaller subject, including a neonatal infant. It is to be appreciated, however, that other embodiments may be configured to encircle a much smaller range of limb sizes, as aspects of the present invention are not limited in this regard.

Various devices may be used as an actuator to constrict the cuff about a subject's limb, or to release the cuff. As illustrated in embodiment of FIG. 8, the actuator includes a pneumatic pump to provide pressurized air to an inflatable cuff through an air hose. The actuator also includes a release valve 20 that, when actuated, opens a passageway between the inflatable cuff and the external environment to allow pressurized air to escape from the cuff, so that the cuff loosens about the subject's limb.

The air pump can comprise any device capable of delivering compressed air. According to some embodiments, the air pump includes a piston compressor, although other types of pumps, like centrifugal pumps and scroll compressor may also be used. The pump may be configured to provide air flow at a rate of between 0.1 to 20 cubic feet per minute, with a head pressure of up to 50 psi, according to some embodiments. However, other flow rates and/or pressures are possible, as aspects of the invention are not limited in this respect.

As discussed above, the actuator may also include a release mechanism to release a cuff from about the subject's limb. In the illustrated embodiment, the release comprises a release valve 20 that is positioned within the controller housing. The release valve, as shown, may be a solenoid that moves rapidly between fully closed and fully open positions to rapidly release air from the cuff and, in turn, to rapidly release the cuff from a subject. According to some embodiments, the same release valve or another release valve may also be actuated to open slowly, such as to adjust the pressure of the cuff or to allow a more controlled release of pressure such as may be required when the subject's blood pressure is measured.

Embodiments of the system may include safety features to allow rapid release of the cuff from a subject's limb. Moreover, some of these embodiments may be readily activated by a subject, such as when the subject feels discomfort. In one embodiment, the safety release 22 includes a large button positioned on or near the cuff. In this regard, the safety release is within reach of the subject. In other embodiments, the safety release may comprise a separate actuator, such as one that may be held in the free hand of the subject. Activating the safety release may cause the release valve of a pneumatic cuff to open, thereby allowing rapid removal of air from the cuff.

The system may also include a continually operating, cuff release mechanism. By way of example, a slow release valve may be incorporated into a pneumatic cuff to provide for a continual, slow release of pressurized air from the cuff. The continual slow release mechanism may provide for the safe release of a subject's limb, even in the face of power failures or other events that may prevent redundant safety features from operating properly. Similar type mechanism may be incorporated into embodiments that do not utilize a pneumatically inflatable cuff, as continual slow release mechanisms are not limited to pneumatic cuffs. The system may also comprise a pressure check valve as a safety feature. Such a valve may operate by releasing pressure above a maximum set point. The maximum set point will be at or above the supra-systolic pressures used during remote ischemic conditioning, and may be but is not limited to 200 mmHg, 210 mmHg, 220 mmHg, 230 mmHg, 240 mmHg, or 250 mmHg. The system may also comprise software and/or hardware components that monitor pressure (e.g., the cuff pressure and/or the subject blood pressure) and preferably read out such pressure measurements whether in real-time or after the remote ischemic conditioning is complete. In this way, deviations in pressure can be identified.

Embodiments of the system include a controller that receives information from a protocol and any other sensors in the system to, in turn, control the actuator to perform RIC. The controller and protocol combination may be implemented in any of numerous ways. For example, in one embodiment the controller and protocol combination may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the functions discussed herein. The one or more controllers can be implemented in numerous ways, such as with dedicated hardware, or with general purpose hardware (e.g., one or more processors) that is programmed using microcode or software to perform the functions recited above. The one or more controllers may be included in one or more host computers, one or more storage systems, or any other type of computer that may include one or more storage devices coupled to the one or more controllers. In one embodiment, the controller includes a communication link to communicate wirelessly, or via electrical or optical cable, to a remote location.

In this respect, it should be appreciated that one implementation of the embodiments of the present invention comprises at least one computer-readable medium (e.g., a computer memory, a floppy disk, a compact disk, a tape, etc.) encoded with a protocol in the form of a computer program (i.e., a plurality of instructions), which, when executed by the controller, performs the herein-discussed functions of the embodiments of the present invention. The computer-readable medium can be transportable such that the protocol stored thereon can be loaded onto any computer system resource to implement the aspects of the present invention discussed herein. In addition, it should be appreciated that the reference to a protocol or controller which, when executed, performs the herein-discussed functions, is not limited to an application program running on a host computer. Rather, the term protocol is used herein in a generic sense to reference any type of computer code (e.g., software or microcode) that can be employed to program a processor to implement the herein-discussed aspects of the present invention.

The system may also comprise one or more sensors 26 that receive information from the subject and/or portions of the system itself. Such sensors may receive information regarding blood flow in any portion of the subject, including the limb that is being treated. These sensors may also receive information regarding other operating parameters of the system, such as air pressure within a pneumatic cuff, direct readings of pressure applied by cuff, or tension within portions of a tension band.

Pneumatic cuffs may include a sensor to measure pressure within the cuff. Cuff pressure is often directly indicative of the pressure that exists within a blood vessel of the limb beneath the cuff. The controller of a system is often programmed to target a particular cuff pressure that is to be maintained during the ischemic duration of a cycle, as is discussed herein. In embodiments that include a pneumatic cuff, the pressure sensor may be positioned anywhere within the pressurized space of the cuff, the air hose, or even within the actuator itself. Pressure sensors may also be positioned on an inner surface of the cuff to directly measure the pressure between the cuff and an outer surface of the subject's limb. In use, the cuff may be oriented such that the pressure sensor is positioned directly above the subject's artery, so as to provide a more direct measurement of pressure at a blood vessel of interest. Reference can be made to Noordin et al. J Bone Joint Surg Am, 2009, 91:2958-2967 which discusses the relationship of cuff width, circumference and pressure on measurements of blood pressure.

In one embodiment, systems may also include one or more vibration and/or ultrasonic sensors 28 to identify Korotkoff sounds. Korotkoff sounds are generally understood to be present when pressures between systolic and diastolic are externally applied to the artery of a subject. Systolic pressure is associated with a pressure value that completely occludes blood flow through a subject's blood vessels, and in this regard, may be used by the system as feedback to identify when pressure in the system is low enough to allow blood flow, or high enough to occlude blood flow.

One or more sensors may be included to confirm the cessation of blood flow or reperfusion in the limb that receives the cuff. For instance, in some embodiments, a pulse oximeter 30 may be positioned on a distal portion of the limb that receives the cuff, such as on a finger or toe of the limb. The pulse oximeter can provide information regarding blood pulsing through the subject's blood vessels and the percentage of haemoglobin that is saturated with oxygen. The pulse oximeter will detect an absence of pulses when blood flow though a limb is not occurring to confirm the occlusion of blood flow. Moreover, the pulse oximeter may also detect the percentage of haemoglobin saturated with oxygen, which will drop as blood flow through the limb ceases. It is to be appreciated that other sensors may also be used to confirm the cessation of blood flow, such as a photoplethysmographic transducer, an ultrasonic flow transducer, a temperature transducer, an infrared detector, and a near infrared transducer, as aspects of the invention are not limited in this respect.

As mentioned above, the system includes a protocol that, through the controller, directs the operation of the system. Embodiments of the protocol include a cycle that comprises cuff actuation, an ischemic duration, cuff release, and a reperfusion duration. In many embodiments of protocols, the cycle may be repeated multiple times. Additionally, some embodiments of the protocol include systolic pressure identification.

The cuff actuation portion of the cycle comprises contracting the cuff about the limb of a subject to occlude blood flow through the limb. Contraction of the cuff is accomplished by the controller reading instructions from the protocol, such as a target set point for cuff pressure, and then by the initiating the controller to bring the cuff to the target set point. Attainment of the target set point may be sensed through any of the herein described sensors and techniques.

During the ischemic phase of the cycle, pressure is maintained about the subject's limb to prevent reperfusion of blood flow through the limb. The length of the ischemic phase, termed the ischemic duration, is typically defined by a doctor, or other medical professional, and is programmed into the protocol. Ischemic duration may be as short as a few seconds, or as long as 20 minutes, or even longer, as aspects of the invention are not limited in this regard. In some embodiments, the ischemic duration varies from cycle to cycle during the same protocol, although in other embodiments, the ischemic duration remains constant.

The controller acts to maintain pressure, applied by the cuff, at a set point above the subject's systolic pressure. Embodiments of the cuff may relax relative to the subject's limb over time, thereby reducing pressure and eventually allowing reperfusion. This may be caused by various factors, including relaxation of muscles in the subject's limb, stretching of the cuff about the limb, air leaks (intentional or unintentional), and the like. To this end, a sensor may provide pressure readings as feedback to the controller. The controller can measure any difference between the set point and the actual pressure reading and can provide any necessary commands to the actuator to compensate for errors.

Various approaches may be used to define an appropriate set point for the controller during the ischemic duration. According to one embodiment, the set point is manually entered into the protocol by the doctor (or other medical professional). Alternately, the doctor may select a set point in terms of the subject's systolic blood pressure. In one embodiment, the set point may be selected as a fixed pressure amount over the subject's systolic blood pressure, such as 5 mmHg, 10 mmHg, 15 mmHg, 20 mmHg, 25 mmHg, 30 mmHg, 35 mmHg, or any other fixed amount above systolic pressure of the subject. In other embodiments, the set point may be defined as a percentage of the subject's systolic blood pressure, such as 101%, 102%, 103%, 104%, 105%, 106%, 107%, 108%, 109%, 110%, 111%, 112%, 113%, 114%, 115% or systolic pressure and other percentages, as aspects of the invention are not limited in this respect. The point above systolic pressure may be set by the medical professional and may be dependent upon several factors including, but not limited to the size of the subject, the size of the subject's limb, the subject's blood pressure, confirmation of blood flow cessation, and the like.

The protocol, according to some embodiments, includes phases to identify the subject's systolic blood pressure. The cuff may be allowed to loosen about the subject's limb, from a point believed to be above systolic pressure, in a systematic manner while sensors are monitoring the limb for the onset of Korotkoff sounds or vibrations. Once the systolic pressure is identified, the protocol may continue in the normal course.

Identification of systolic pressure may optionally occur at any time during a protocol, or not at all. According to some embodiments, each cycle begins with the identification of the subject's systolic blood pressure. In other embodiments, systolic pressure may be identified only once during an initial portion of the protocol. In still other embodiments, systolic pressure may be identified as the cuff is released during the cuff release portion of each cycle. Still, as discuss herein, systolic pressure may not be identified at all during a protocol, as aspects of the invention are not limited in this regard.

The system can be configured to adjust the pressure set point during the ischemic duration. As discussed herein, the system may include sensors that detect the onset of reperfusion. As an example, this may be accomplished by detecting the presence of Korotkoff sounds or vibrations. The presence of Korotkoff sounds during an ischemic duration can indicate that either cuff pressure has fallen below systolic or that systolic pressure has risen above the set point that was previously above systolic pressure. Other devices may additionally or alternatively be used including for example devices on digits that detect the presence or absence of flow. In such a situation, the controller may adjust the set point based on the newly identified systolic pressure and/or other information and in this regard, can identify and prevent unwanted reperfusion that might otherwise occur.

The cuff release portion of a cycle occurs at the end of the ischemic duration and includes release of the cuff to a point below diastolic pressure. According to some embodiments, cuff release comprises releasing the pressure or tension of the cuff. In embodiments that utilize a pneumatic cuff, this may simply be associated with moving an air release valve to the fully open position to allow a rapid reduction in cuff pressure and a corresponding rapid relaxation of the cuff about the subject's limb. However, it is to be appreciated, that in other embodiments, that cuff relaxation may occur in a slower, more controlled manner, as aspects of the invention are not limited in this respect. Additionally, as discussed herein, the cuff release may be accompanied by monitoring for the onset of Korotkoff sounds or vibrations to identify or confirm the systolic pressure of the subject.

The reperfusion duration follows the cuff release in embodiments of the cycle. Reperfusion through the limb is allowed for a period of time termed the reperfusion duration. Much like the ischemic duration, reperfusion may be allowed for varied lengths of time, as short as a five seconds, one minute or more, and as long as 20 minutes, or even longer. The reperfusion duration may remain constant from cycle to cycle during a common protocol, or may vary between each cycle, as aspects of the invention are not limited in this respect.

The protocol may comprise any number of cycles. As discussed herein, a common cycle may simply be repeated a plurality of times, such as two, three, four, or more times, to complete a protocol. Alternately, the cycles of a protocol may be programmed with different parameters, such as different ischemic durations, reperfusion durations, pressure set points during the ischemic duration, and the like.

In some embodiments, the system may include a data logging feature that records the system parameters, such as cuff pressure or tension, during all phases of a protocol. Date of time of operation may also be recorded. Other features, such as personal information to identify the subject, may also be recorded by the system.

Embodiments of the system may incorporate various features to inform the subject or medical professional about the progress of the protocol. Audible or visual indicators may accompany any of the phases of the protocol. By way of example, a clock may show either the amount of time that has elapsed or that remains for a given portion of the protocol or the entire protocol. Embodiments may also include other features to keep the subject and/or medical professional informed, as aspects of the invention are not limited in this regard.

According to some embodiments, the system includes features to prevent tampering or accidental reprogramming by a subject. By way of example, in some embodiments, the reprogrammable features may only be accessed after entering a code. This can prevent a subject from mistakenly reprogramming the protocol or otherwise interfering with the operation of the system. It is to be appreciated that other devices may also be used to prevent accidental reprogramming, such as electronic keys, mechanical locks and the like.

The system may be configured for use is a variety of environments. By way of example, the system may be mounted on a portable stand with casters to facilitate easy movement. The stand may position the controller, user interface, and connections to the cuff at a convenient height for the subject. In other embodiments, the system is configured for portable use. In such embodiments, the system may be configured for ready placement into a suitcase for easy transport.

Figure 10:
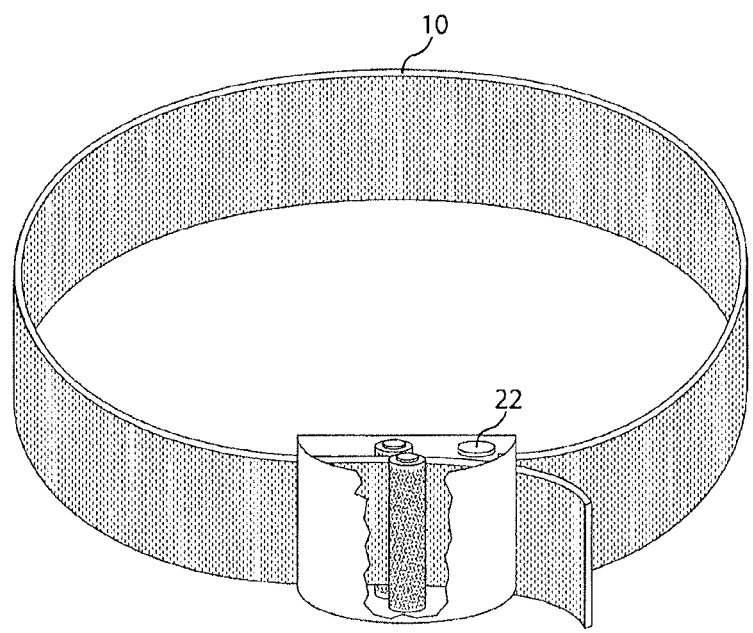
FIG. 10 is a perspective view of an alternate embodiment of a cuff configured to contract about the limb of a subject.

The system is also not limited to components illustrated in the embodiment of FIG. 1. By way of example, according to other embodiments, like that illustrated in FIG. 10, cuffs may be configured to constrict a subject's limb through alternative mechanisms. In the illustrated embodiment, the cuff is configured as a band having a ratcheting mechanism positioned at one end. In use, the band is wrapped about the limb of a subject with the free end of the band passing through the ratcheting mechanism. In such an embodiment, the actuator may comprise a mechanism that pulls the free end of the band further through the ratcheting mechanism to retract the cuff about the limb, or that frees the ratcheting mechanism to release the band to, in turn, release the band from the limb. Still other mechanisms, such as tourniquet mechanisms, are possible, as aspects of the invention are not limited in this respect.

As described above with reference to FIG. 10, some embodiments may have a cuff that comprises a band that does not inflate, but rather is tightened about a subject's limb by another mechanism. In such embodiments, the actuator may comprise a tensioning mechanism configured to move one end of the band relative to other portions of the band so as to place the band in tension. As shown, the mechanism can include opposed rollers held in close proximity to one another within a housing. The housing includes a slot for receiving a free end of the band and a fixation point for fixed attachment to the opposite end of the band. The free end of the band is passed into the slot and between the rollers. The rollers may be mechanically actuated to rotate relative to one another, such as by an electric motor, to pull the free end through the housing and thus tighten the band around a subject's limb.

The tensioning mechanism may include opposed rollers mounted on a ratcheting, free wheel mechanism. The freewheel mechanism allows the band to be pulled through the slot in one direction with minimal resistance so that the band may be pulled rapidly to a snug position about a subject's limb. The free wheel mechanism also prevents the band from moving through the slot in the loosening direction, unless the mechanism is released or the opposed rollers are actuated. It is to be appreciated that not all embodiments will include a free wheel mechanism, as aspects of the invention are not limited in this regard.

The opposed rollers rotate in either direction to tighten and loosen the band during use. When required, the rollers may rapidly rotate until the band achieves a particular tension. The rollers may further be actuated to make minor adjustments to the tension in the band during use. When the cuff is to be released from the subject's limb, a ratcheting mechanism or clutch may be released such that the opposed rollers are allowed to move freely, thus rapidly releasing tension.

The system and/or device may comprise disposable components to prevent contamination between subjects and to avoid the need to sterilize the system or device between subjects. The entire system or device may be disposable or one or more of its components may be disposable. Disposable component include but are not limited to the cuff(s) of the system and/or sleeves or liners for the cuff(s).

Aspects of the invention are not limited to the embodiments of cuffs illustrated herein.

EXAMPLES

Materials and Methods

Animals. Fifty eight week-old male Sprague-Dawly (SD) rats, weighing between 250 g and 280 g (Experimental Animal Center, Fudan University, Shanghai, P.R. China) were studied. The animal research study protocol was in compliance with 'The Guide for the Care of Use of Laboratory Animals' published by the National Institute of Health (NIH Publication No. 85-23, revised 1996) and approved by the Animal Care Committee of Shanghai Sixth Hospital, Shanghai Jiao Tong University School of Medicine. All the rats were housed for two weeks for an acclimatization period before the experiments.

Surgical Preparation. After anesthesia with sodium pentobarbital (40 mg/kg, IP) and endotracheal intubation, animals were ventilated (Animal Respirator DW-2000, Aloctt Biotech, Shanghai, P. R. China) with room air. The heart was exposed through a thoracotomy at the left fourth intercostal space. The left anterior descending coronary artery (LAD) was encircled by a 6-0 prolene suture 1 to 2 mm below the tip of the left atrial appendage and its ends were threaded through a polyethylene tubing (PE-50) to form a snare for reversible coronary artery occlusion. Prior to LAD occlusion, the animals were anticoagulated (150 U/Kg sodium heparin) and received an intravenous injection of lidocaine (4 mg/Kg). Cardiac ischemia was confirmed by a pale area below the suture or ST-T elevation shown in ECG, while reperfusion was characterized by rapid disappearance of cyanosis and vascular blush. At the end of the protocol, the snare was removed, the chest closed, and the animals allowed to recover, and they were given tamgesic (0.03 mg/kg) immediately before they gained consciousness.

Experimental Protocol. After anesthesia, all rats were randomly assigned to the following six experimental groups:

1) MI group (MI control), MI was created with 45 minutes LAD ligation followed by reperfusion for long term observation;

2) Single remote ischemic post-conditioning (sPost) group (also referred to herein as rIPerC), during the ischemia reperfusion injury surgical procedure, while the animals were anesthetized remote ischemic post-conditioning was delivered starting 20 minutes before the end of index ischemic period by occluding hind limb blood flow with a torniquet tightened around the upper thigh for 4 cycles of 5 minutes occlusion followed by 5 minutes release. The limb ischemia was confirmed by pallor and cyanosis of the lower limb below the torniquet;

3) Delayed post-conditioning (dPost) group, the delayed remote post-conditioning was delivered on day 4 (72 hours after reperfusion). Rats were anesthetized again with smaller dosage of sodium pentobarbital (30 mg/Kg). The remote post-conditioning was delivered the same way as described above. Tamgesic (0.03 mg/kg) was also given before they regained consciousness;

4) Repetitive remote post-conditioning (rPost) group (also referred to herein as rPostC), after the initial remote post-conditioning (identical to group 2), post-conditioning was repeated every three days for 28 days, and therapy was delivered the same way as described in dPost group rats;

5) Intensive remote post-conditioning (iPost) group (also referred to herein as iPostC), after the initial remote post-conditioning (identical to group 2), the same remote post-conditioning therapy as described above was repeated every day for 28 days;

6) Sham group, rats underwent sham operation without suture tie-down. All the surviving rats that completed the observation period were sacrificed either on day 4 (72 hours after reperfusion), I also have marked this on protocol figure), or on day 28 after reperfusion, respectively for testing outlined below, and detailed in FIG. 1.

For day 4 and day 28 studies, animals assigned to the remote ischemic post-conditioning therapy on either day 4 or day 28 were euthanized 2 hours after the episode of post-conditioning. Both echocardiographic and invasive hemodynamic examination (described as below) was performed to evaluate the remodeling process immediately before euthanization.

After euthanization, whole blood was then collected from inferior vena cava and the heart was harvested. A careful autopsy was performed for each rat, including those who experienced sudden cardiac death, particularly in regard to possible cardiac rupture. After autopsy, LV weight was recorded for hearts obtained from day 28 and the ratio of LV weight to body weight (LVMI) was calculated. One cross-section of LV myocardial tissue at the level of the papillary muscles, approximately 5 mm, was collected and fixed in 4% formalin followed by paraffin embedding for the histology examination. The remaining LV tissue was snap frozen in liquid nitrogen and stored at −80° C. for later analysis.

Survival Study. To evaluate the survival rate, another total 250 rats were assigned to MI group, RIPerC group, rPostC group, iPostC group and SP group (50 rats for each group) while 25 sham operated rats acted as controls. All the rats were rigorously monitored for 12 weeks. A careful autopsy was performed for each rat searching for the cause of sudden death, especially in reference to cardiac rupture. Survival rate was analyzed to evaluate the long term benefits of the treatments.

Echocardiography and Hemodynamic Study. Transthoracic echocardiography was performed only on day 28 after MI. using ultrasonic system equipped with a 15-MHz probe (Acuson Sequoia 512). Both two-dimensional and M-mode echocardiography was obtained after the induction of anesthesia. LV end diastolic diameter (LVEDD) and LV end systolic diameter (LVESD) was measured in short axis view at papillary muscle level. The fractional shortening (FS) was also calculated. All the values were averaged over five consecutive cardiac cycles and measurements were analyzed by two independent researchers blinded to treatment protocol. Thereafter, cardiac catheterization was performed in animals for hemodynamic study. The right carotid artery was cannulated with a pre-heparinized fine polyetheylene tube connected to a fluid-filled pressure transducer (MPA-CFS, Alcott Biotech, Shanghai, China) and the tube was then advanced into the left ventricle. Heart rate (HR), left ventricular peak systolic and end-diastolic pressure (LVEDP) and the maximal rates of rise and fall in LV pressure ($dP/dt_{max}$ and $dP/dt_{min}$, respectively) were recorded.

Myocardial Infarct Size Determination. On day 4 (72 hours after reperfusion), the LAD was re-occluded and 1 ml 1% Evan's blue was perfused into the aorta and coronary arteries. The heart was then isolated, perfused with PBS and sliced transversely in a plane perpendicular to the apical-basal axis into 8 mm thick sections. Heart sections were then incubated in 1% 2,3,5-triphenyltetrazolium chloride (TTC) (Sigma) for 5 to 10 min at 37° C. The infarct area (pale), the area at risk (red), and the total LV area from each section were measured using Image J software. Infarct size, expressed as a percentage, was calculated by dividing the sum of infarct areas weight from all sections by the sum of LV risk area weight from all sections and multiplying by 100.

To measure infarct size 28 days after MI, the LV area was estimated using a slice obtained from the central part of the myocardium at the level of the papillary muscles. The infarct (expressed as fibrotic area) perimeter was traced and the size of MI was normalized to LV area using the following equation: percentage Infarct perimeter (IP)=Circumference of Infarct Scar/[(Epicardium Perimeter+Endocardium Perimeter)/2]×100%[22].

Histological Analysis. Deparaffinized tissue sections were prepared for immunohistochemical staining. First antibody against Myeloperoxidase (MPO, 1:50 dilution, Abcam), against ED-1 (a specific marker for macrophage, 1:100 dilution. Chemicon) and Monocyte chemoattractant protein-1 (MCP-1, 1:100 dilution, Abcam) were performed for neutrophil and macrophage infiltration quantification, using heart tissue obtained from day 4. Antibody against 8-Hydroxyguanosine (8-OhdG, 1:300 dilution, Abcam) was also used for quantifying oxidative stress mediated DNA injury, using heart tissue obtained from day 28. Sections incubated with secondary antibody alone served as negative control. All sections were counterstained with hematoxylin.

Collagen deposition in the border area was quantified by Masson-staining and analyzed by using Image J software and expressed as the average percentage collagen staining of 10 randomized high power field.

In addition, the hematoxylin-eosin stained sections from the central portion of the LV was obtained to evaluate myocyte cross-sectional area (CSA) in those centrally-nucleated cells cut transversely. The CSA was measured and averaged of 50 cells in the posterior wall (non-infarcted area) of the LV from each sample, and a total four samples were analyzed for each group.

Western Blot. Equal amounts of protein (50 µg) were separated on 8-16% Tris-glycine gel (Novex, Invitrogen, CA, USA) and transferred to a PVDF membrane. After blocking with 5% skim milk, primary antibody against phospho-Smad2, phospho-IκB-α (Ser32), IκB-α, phospho-NF-κB-P65, NF-κB-P65 (Cell Signaling Tech, USA), and TGF-β1 and Smad2 (Santa Cruz, USA) were incubated overnight at 4° C. followed by incubation with horseradish peroxidase conjugated secondary antibody either anti-mouse or anti-rabbit (1:2000). Immuno-reaction was finally visualized using an ECL detection Kit (Amersham, Beverly, Mass., USA). All the protein expression level was adjusted for GAPDH intensity (Cell Signaling Tech, USA). Bands were quantified by densitometry using the software of Image J (version 1.41, NIH, USA).

Real Time RT Polymerase Chain Reaction. Total RNA was prepared from 150 mg of LV tissue using Trizol reagent (Invitrogen) followed by chloroform extraction and isopropanol precipitation. Genomic DNA was eliminated by incubating with DNase I (0.1 µl$^{-1}$, 37° C.) for 30 min followed by acid phenol-chloroform extraction. RNA was quantified by spectrophotometric absorbance at 260 nm, with its purity confirmed by $A_{260}/A_{280}$ ratio and integrity evaluated by ethidium bromide staining on a denaturing agarose gel. Total RNAs (2 µg) were then reverse transcribed using oligo(dT) primer and Superscript II reverse transcriptase (RT, Invitrogen).

Real time PCR quantification was performed starting with 12.5 ng cDNA and both sense and antisense primer at 900 nM concentration (Invitrogen) in final volume of 25 µl, using SYBR Green master mix (Applied Biosystem). Fluorescence was monitored and analyzed in a GeneAmp 7000 detection system instrument (Applied Biosystems). The PCR reactions were cycled 42 times by a three-step cycle procedure (denaturation 95° C., 15 s; annealing 60° C., 30 s; extension 72° C., 30 s) following the initial stage (95° C., 10 min). A ΔCt value was obtained to quantify the mRNA levels and normalized with an endogenous control (b-tubulin mRNA) for each sample. A relative quantification ΔΔCt method was used for comparison between groups. Oligonucleotide primers were designed using Primer Express software (Applied Biosystems).

The primers used were listed as follows:

α-MHC, sense
(SEQ ID NO: 1)
(CTGCTGGAGAGGTTATTCCTCG)
and antisense
(SEQ ID NO: 2)
(GGAAGAGTGAGCGGCGCATCAAGG);

β-MHC, sense
(SEQ ID NO: 3)
(TGCAAAGGCTCCAGGTCTGAGGGC)
and antisense
(SEQ ID NO: 4)
(GCCAACACCAACCTGTCCAAGTTC);

ANP, sense
(SEQ ID NO: 5)
(CTCTGAGAGACGGCAGTGCT)
and antisense
(SEQ ID NO: 6)
(TATGCAGAGTGGGAGAGGCA);

β-tubulin, sense
(SEQ ID NO: 7)
(TCACTGTGCCTGAACTTACC)
and antisense
(SEQ ID NO: 8)
(GGAACATAGCCGTAAACTGC).

Determination of Malondialdehyde (MDA) Level. Myocardium obtained from the area at risk was homogenized in 1.0 ml of 20 mmol/L Tris-HCl, pH 7.4, containing 5 mmol/L butylated hydroxytoluene. Lipid peroxides were assayed using a commercial available kit (Cat#437639, Calbiochem) according to the manufacturer's introduction, and level of MDA was expressed as µM per gram protein.

Cytokine Levels. Plasma levels of interleukin TNF-α and IL-1β were evaluated by use of commercially available solid-phase sandwich ELISA kits (R&D Systems, Minneapolis, USA) according to the manufacturer's introduction. The detection limits of each assay were as follows: TNF-α, 16 pg/ml and IL-1β, 10 pg/ml.

Statistics. All values were expressed as mean±SD. All data analysis was performed with the use of SPSS 13.0 statistical software. One-way ANOVA followed by multiple comparisons with Student-Newman-Keuls test was used to determine the effects of treatments on the various parameters. Survival rates during follow up among the six groups were analyzed by standard Kaplan-Meier analysis, and a statistical comparison between survival curves was made with the log-rank test. Fisher's exact method is used to analyze the differences in survival rate between the groups. Statistical significance was defined as $P<0.05$.

Results

Figure 11A:
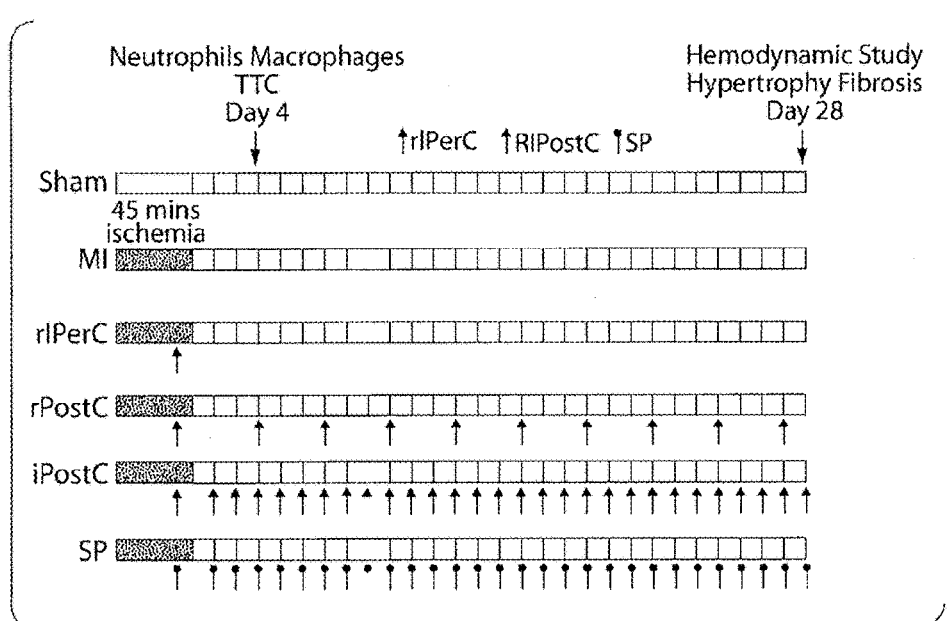
FIG. 11A is a schematic diagram for the treatment groups.
Figure 11B:
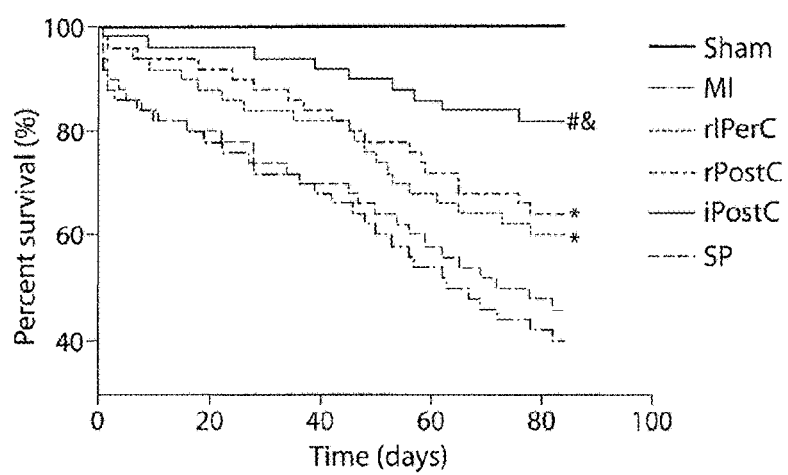
FIG. 11B shows Kaplan Meier curves (survival rates) over an 85 day period following an MI for a sham group, an MI group that received no treatment, an rIPerC group that received RIC during the ischemic phase of the MI, an rPostC group that received RIC during the ischemic phase of the MI and every three days thereafter, an iPostC group that received RIC during the ischemic phase of the MI and every day thereafter, and an SP group that received sodium pentobarbital to control for the effects of the repeated anaesthesia wherein * denotes $P<0.05$ vs. MI group, wherein # denotes $P<0.001$ vs. MI group, and wherein & denotes $P<0.05$ vs. rIPerC group.

Improved Survival Rate by Intensive Post-Conditioning. During the 84 day observation period, rIPerC (or sPost), rPostC (or rPost) and iPostC (or iPost) resulted in improved survival rate compared with MI and SP groups ($P<0.05$, for all). Interestingly, the improved survival rate was apparent as early as 28 days after MI only in the iPostC group whereas in rPostC group this effect was not observed until 56 days after MI. Furthermore, on day 84 iPostC was associated with improved survival rate compared with RIPerC and rPostC treatments ($P<0.05$, respectively). Daily delivery of sodium pentobarbital did not offer any beneficial or adverse effects during the observation period compared with MI group ($P>0.05$) (FIG. 11). Autopsy in those animals who died showed no incidence of cardiac rupture in the treated groups, 1 in the SP group and 1 in the MI group, with no statistical significance between the different groups ($P>0.05$, respectively).

Early Phase of Protection Against Reperfusion Injury. There was a tendency to reduced sudden death during the first seventy-two hours in the sPost, rPost and iPost treated groups compared with MI group, however it was not statistically significant (See Table, $P>0.05$, respectively). Thorough autopsy examinations did not reveal any findings of cardiac rupture in any of the animals. Infarct size was quantified for 8 rats from each group. Area at risk delineated by Evans blue was similar between the five groups (data not shown). There was a significant decrease in infarct size in sPost group rats (35.63±4.21%), rPost group rats (33.88±3.52%) and iPost group rats (31.88±4.82%) (all $P<0.05$), however, the infarct size was not significantly different between these three Post groups ($P>0.05$, respectively), indicating that repetitive remote post-conditioning treatment has no additional effect on infarct size over a single episode of post-conditioning. In contrast, compared with MI group (50.5±4.11%) dPost when delivered 2 hours before euthanization (on day 4) failed to modify infarct size (42±4.54%, $P>0.05$).

Figure 2A:
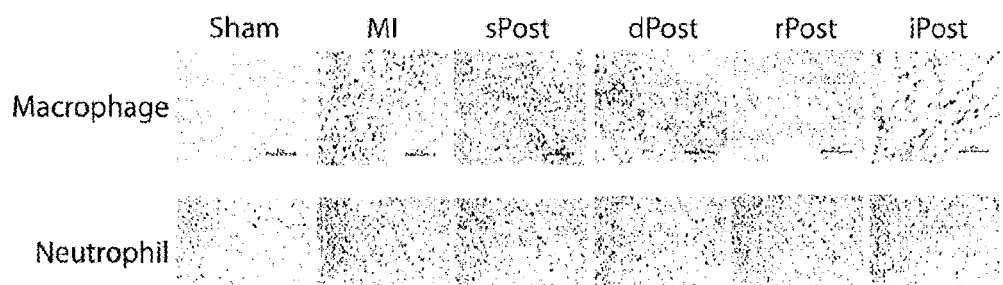
FIG. 2A shows representative photomicrographs from each group of rats, showing numbers of macrophages (upper panels) and neutrophils (lower panels) infiltrating the infarction zone of the heart on day 4 after MI (magnification ×400, scale bar=50 µm)
Figure 2B:
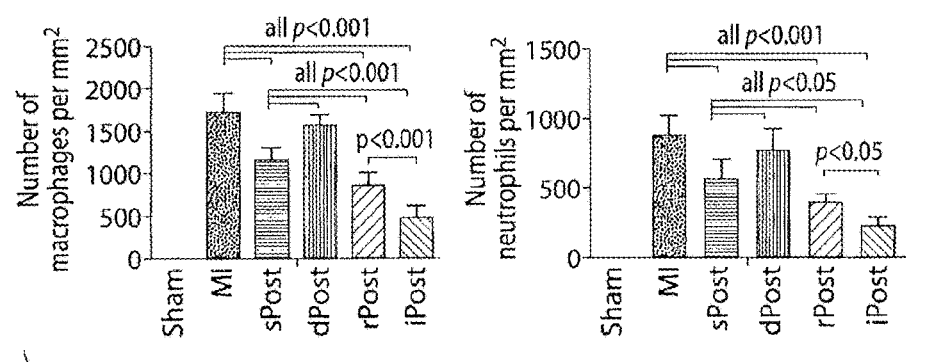
FIG. 2B is a bar graph showing a quantitative analysis of the number of infiltrating macrophages (positive ED-1 staining) and neutrophils (positive MPO staining) in the infarcted area.

Early Phase Inflammatory Response Modulated by Post-Conditioning. On day 4 (72 hours after reperfusion), five hearts were collected from each group respectively for immunohistochemical staining, macrophages and neutrophils infiltration into the infarcted area was minimal in the sham group using antibody targeting ED-1 and MPO (FIG. 2A), respectively. There was intensive infiltration by both macrophages and neutrophils detected in infarcted myocardium (ED-1 cells, 1722±217/mm$^2$; MPO cells, 880±144/mm. $p<0.001$, respectively), which was attenuated in sPost rats ($p<0.001$, respectively; FIG. 2B). Macrophage and neutrophil infiltration was further attenuated by rPost and iPost ($p<0.001$, respectively) with the greatest effect detected in iPost group rats (($p<0.001$; FIG. 2B).

Figure 2C:
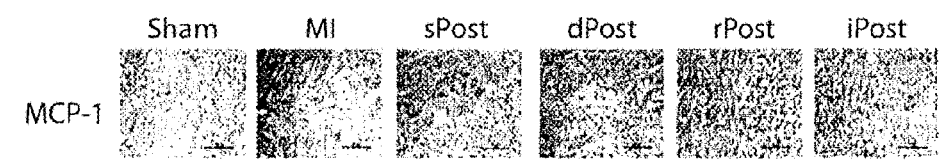
FIG. 2C shows representative heart tissue slices of MCP-1 staining (shown in brown) in the border zone area from each group of rats (magnification ×400, scale bar=50 µm), wherein data are expressed as mean±SD, with the same abbreviations as above.

The expression level of MCP-1 in the infarcted area showed exactly the same pattern as the macrophage and neutrophil infiltration, demonstrating a dose-dependent effect of rIPost on inflammatory cell responses ($p<0.001$, respectively; FIG. 2C). dPost when delivered 2 hours earlier before examination did not show any modification in inflammatory responses (FIG. 2).

Late Phase Protection by Post-Conditioning. There were fewer survivors on day 28 in the MI group and dPost group compared with sham group ($P<0.05$, respectively), whereas sPost and repeated post-conditioning (rPost and iPost) treated groups rats showed no significant difference in comparison with sham group rats (See Table, $P>0.05$, respectively). The infarct size in the survivors to 28 days, demonstrated a similar pattern as on day 4 ($p<0.05$, respectively, Table 1).

Figure 3A:
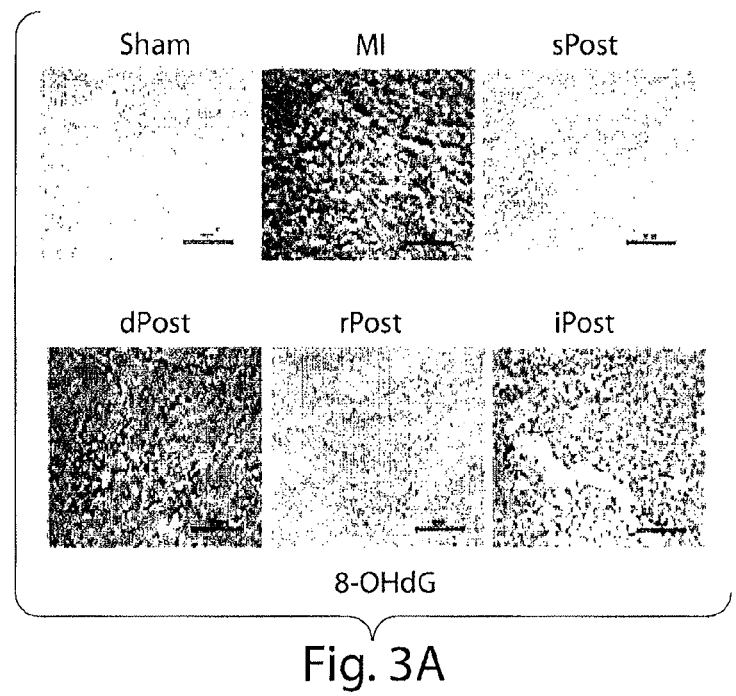
FIG. 3A shows photomicrographs of left ventricular tissue sections with immunostaining targeting 8-hydroxydeoxygaunosine (8-OHdG, shown in brown staining) selected from each group of rats on day 28 (magnification ×400, scale bar=50 µm)

Late Phase Oxidative Stress and Inflammatory Response. DNA damage induced by oxidative stress was evaluated by 8-OHdG immunostaining. The expression of 8-OHdG was increased in MI rats on day 28, rIPost also resulted in a significant dosage dependent reduction in 8-OHdG intensity (FIG. 3A), whereas dPost did not affect the 8-OHdG expression (FIG. 3A).

Figure 3B:
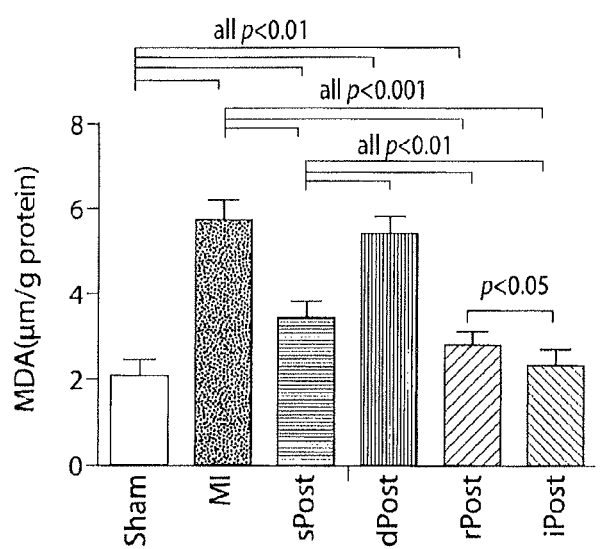
FIG. 3B is a bar graph showing a quantification of myocardial MDA concentrations in each group on day 28.
Figure 3C:
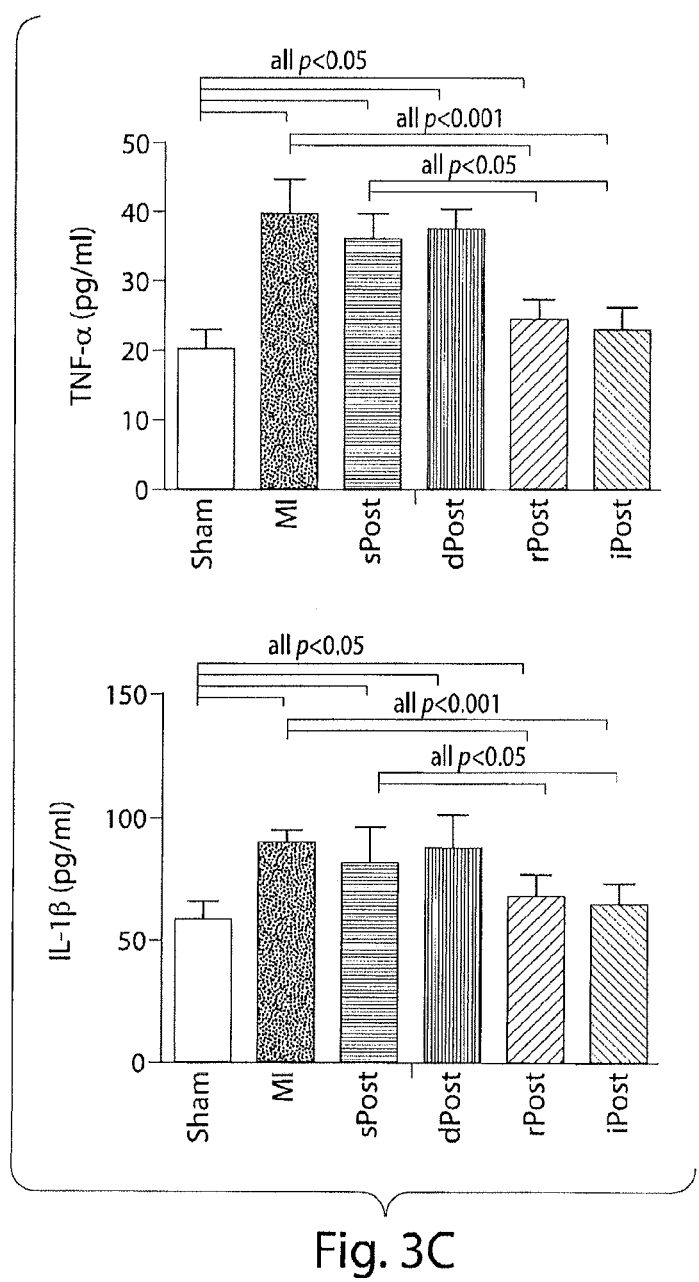
FIG. 3C is a bar graph showing a quantitative analysis of plasma TNF-α (FIG. 3A) and IL-1β (FIG. 3B) levels in each group of rats on day 28 after MI, wherein data are expressed as mean±SD, with the same abbreviations as above.

MDA measurement recapitulated the changes of intensity of 8-OHdG (FIG. 3B). However, while sPost did not modify TNF-α and IL-1β levels on day 28 ($p>0.001$, respectively), they were attenuated by repeated by both iPost and rPost groups, and to the same degree ($p<0.001$, respectively, FIG. 3C).

Figure 4A:
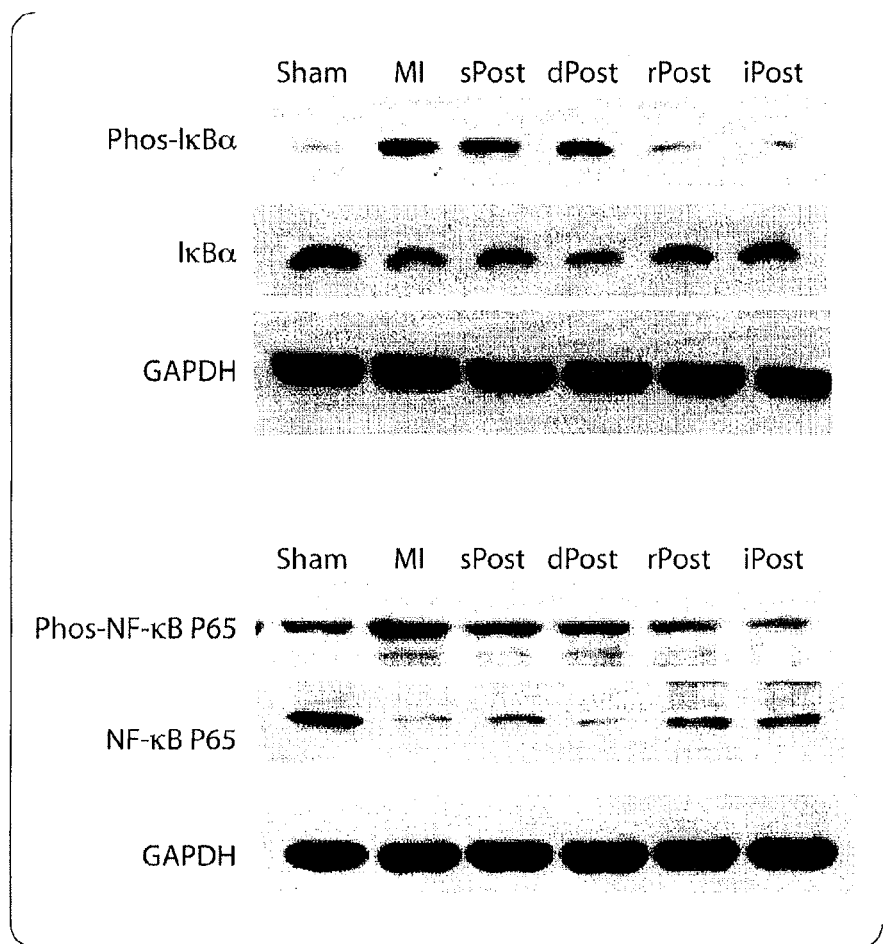
FIG. 4A shows representative western blot bands showing phospho-IκB$_α$, IκB$_α$ and GAPDH (on the left side) and phospho-NFκB P65, NFκB P65 and GAPDH (on the right side) from each group of rats.
Figure 4B:
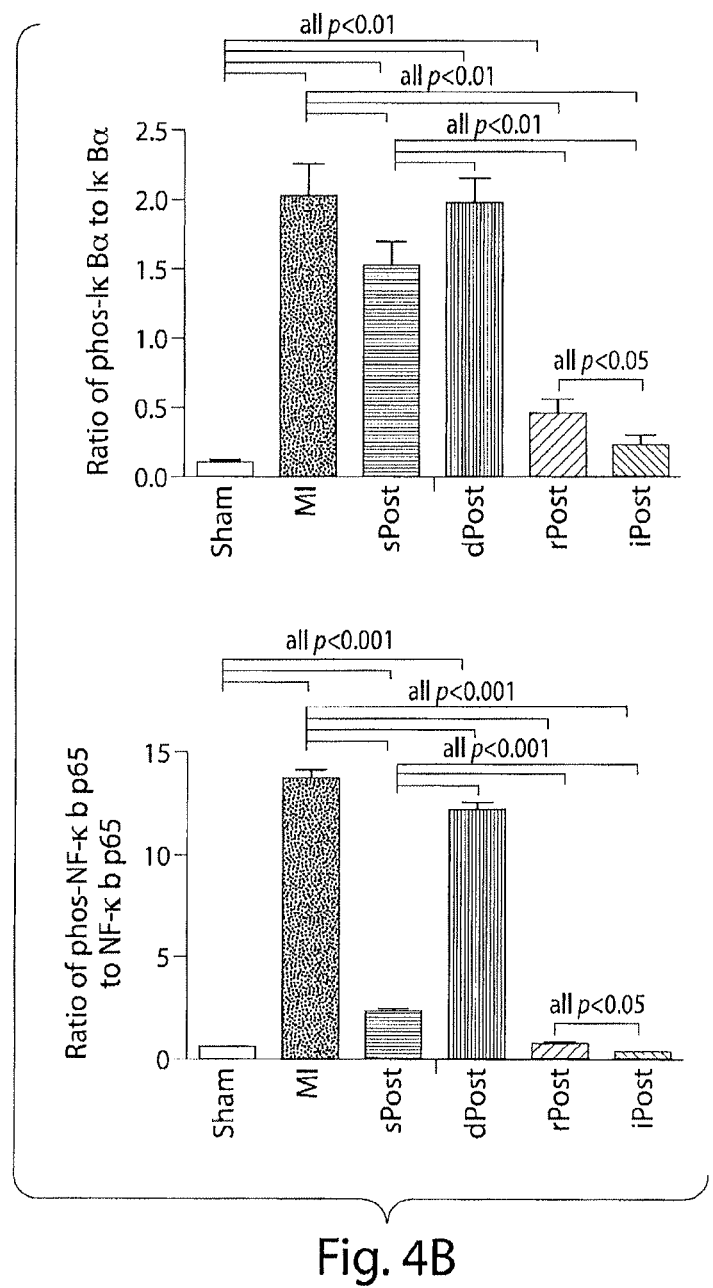
FIG. 4B is a bar graph showing the quantification of ratio of the phospho-IκB$_α$ over IκB$_α$ protein expression and phospho-NFκB P65 over NFκB P65 protein expression (GAPDH as a loading control), wherein data are expressed as mean±SD, with the same abbreviations as above.

Activation of Transcription Factor NF-κB. By comparison with the MI group, sPost was associated with less IκBα and NF-κB p65 phosphorylation. Both rPost and iPost were associated with a further decrease in the degree of IκBα and NF-κB p65 phosphorylation ($p<0.001$, respectively), with iPost group rats showing the lowest activation of NF-κB signaling ($p<0.01$, respectively, FIG. 4).

Figure 5A:
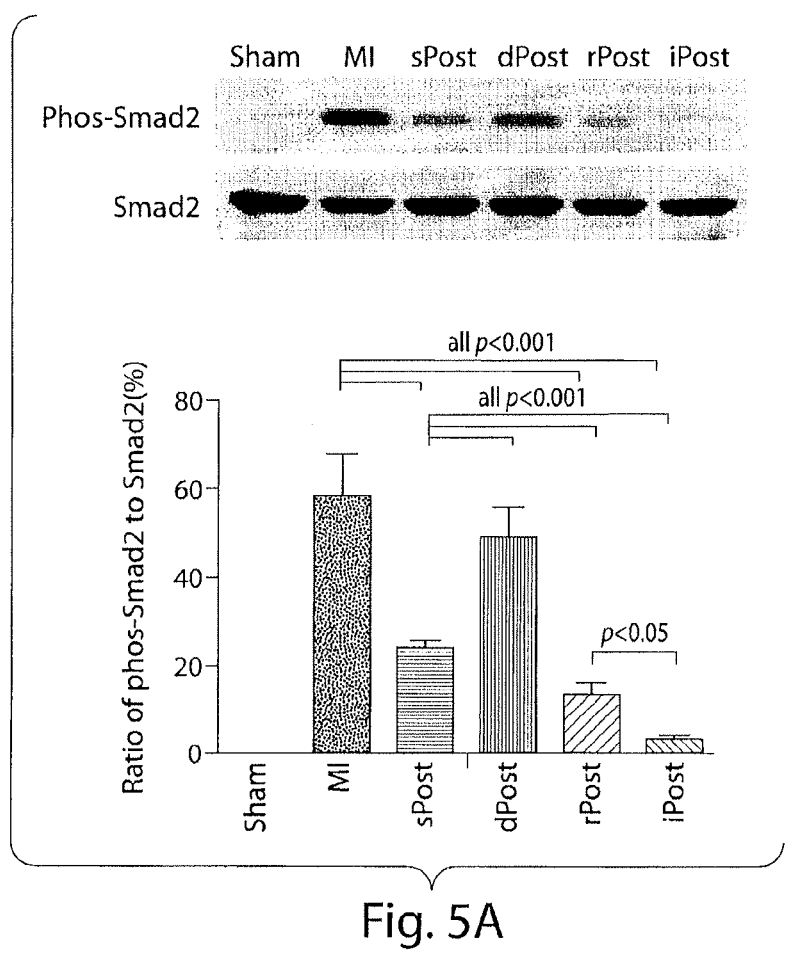
FIG. 5A shows representative Western blot bands for phospho-Smad2 and Smad2, and a bar graph showing the ratio of phosphor Smad2 over total Smad2 protein expression.
Figure 5B:
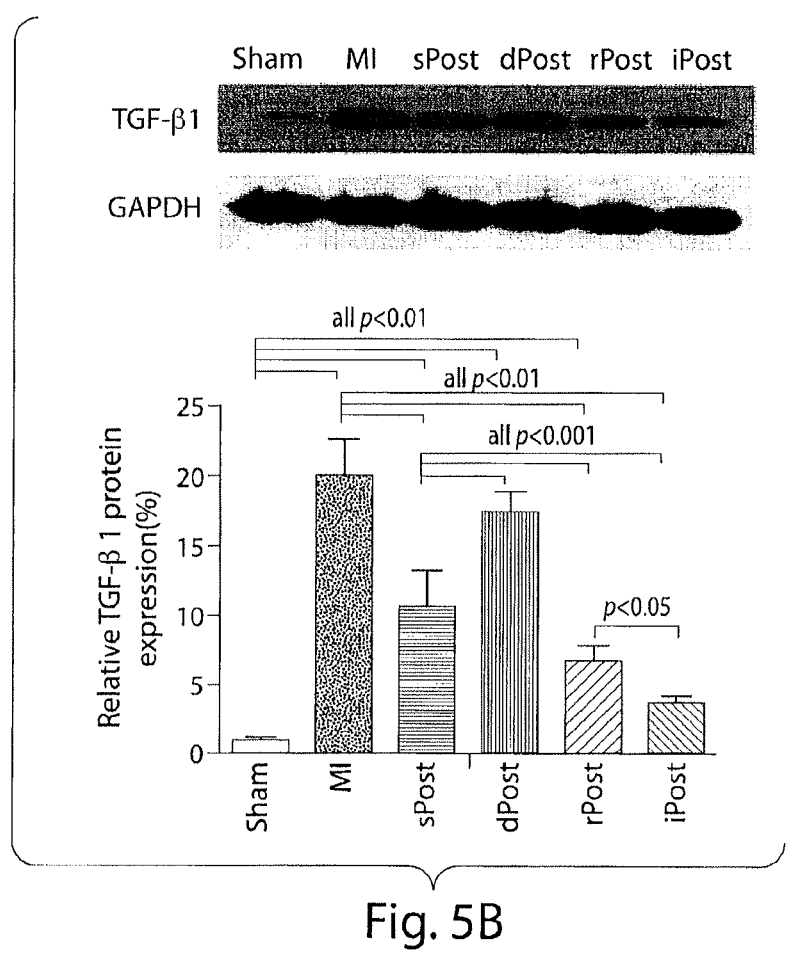
FIG. 5B shows Western blot bands for TGF-β1 and GAPDH from each group of rats and a bar graph showing relative TGF-β1 protein expression (%), wherein GAPDH is for protein loading control and data are expressed as mean±SD, with the same abbreviations as above.
Figure 6:
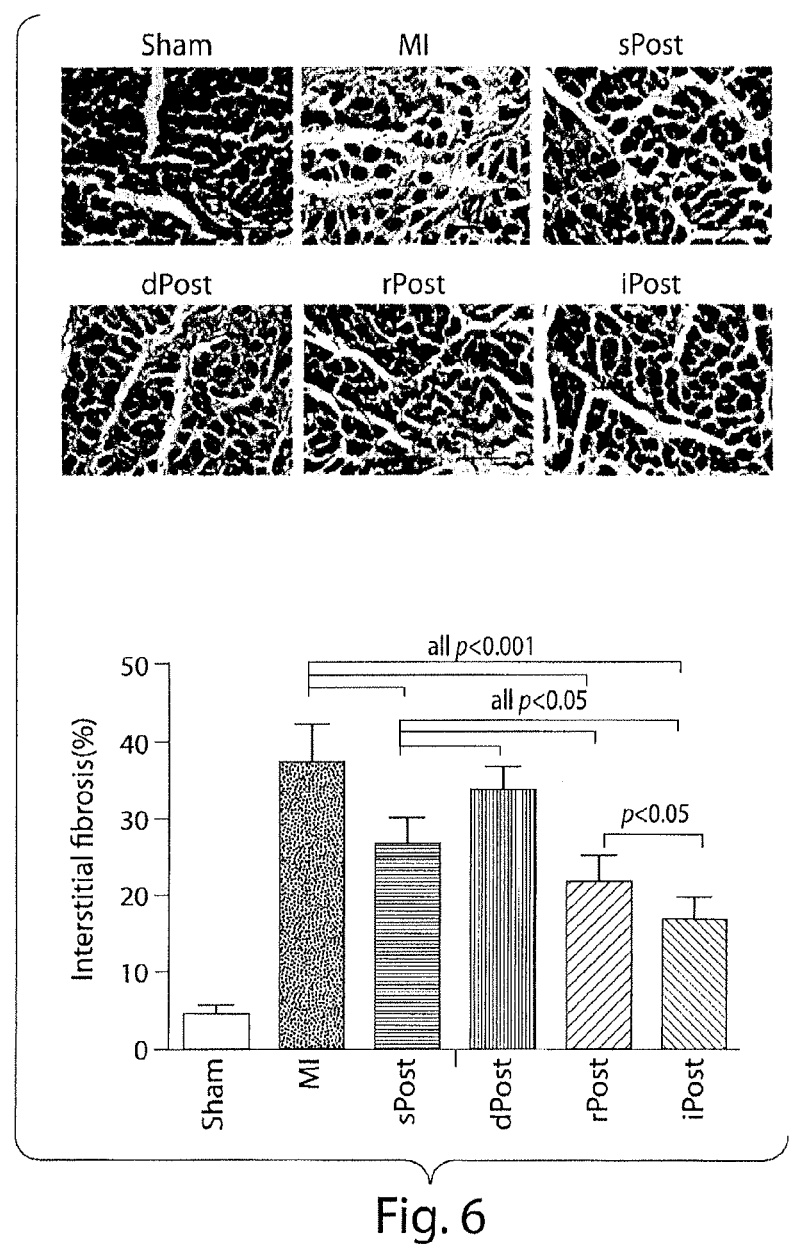
FIG. 6 shows representative sections with Masson's trichrome staining (stained in blue, magnification ×400, scale bar=50 µm) within the border zone area of each group of rat hearts, and a bar graph showing quantitative analyses of the extent of the interstitial fibrosis for each group wherein data are expressed as mean±SD, with the same abbreviations as above.

Fibrosis Responses Modulated by Repeated Post-Conditioning. The modulation of TGF-β1/Smad2 signaling activation by rIPost was consistent with the beneficial effects pattern of the NF-κB signaling activation (FIG. 5), which was further supported by attenuated interstitial fibrosis shown in Masson trichrome staining (FIG. 6).

Hypertrophic Response. The increase in LVMI seen in the MI group was attenuated by sPost ($p<0.05$; Table). A further decrease was detected in both rPost and iPost, with the lowest LVMI observed in iPost ($p<0.001$, respectively, Table).

Figure 7A:
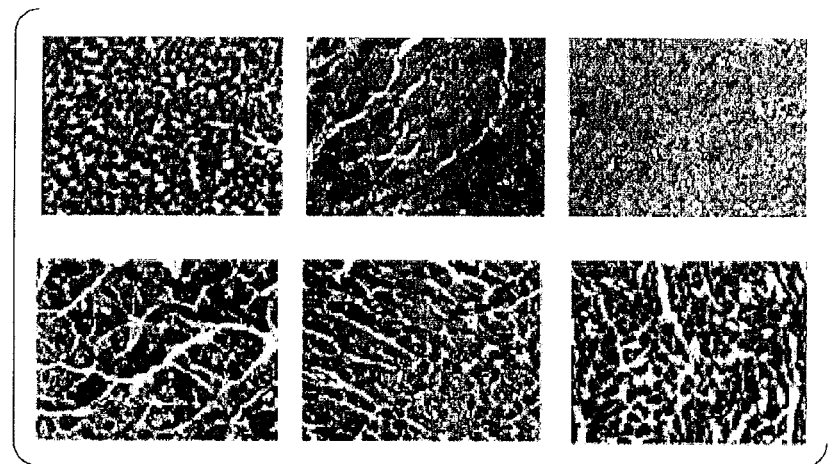
FIG. 7A shows representative photomicrographs to show variations of the cross sectional area of cardiomyocytes stained with hematoxylin and eosin (magnification ×400)
Figure 7B:
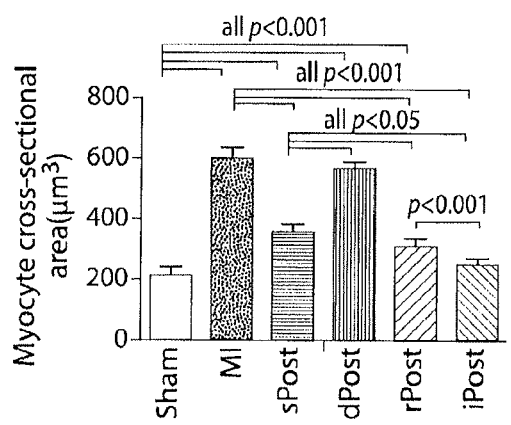
FIG. 7B is a bar graph showing quantitative morphometric analysis of cardiomyocyte cross sectional area ($mm^2$)
Figure 7C:
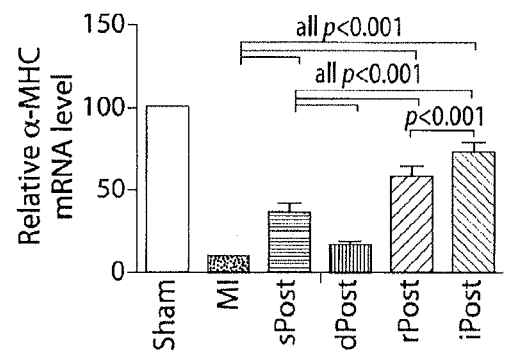
FIG. 7C is a bar graph showing the mRNA expression of α-MHC.
Figure 7D:
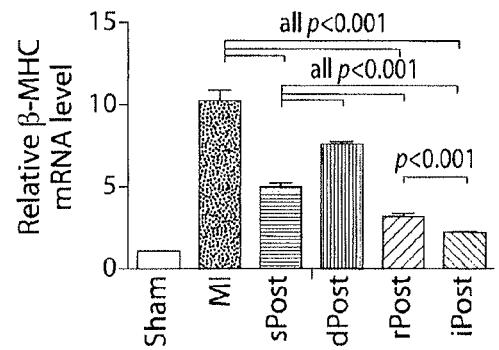
FIG. 7D is a bar graph showing the mRNA expression of β-MHC.
Figure 7E:
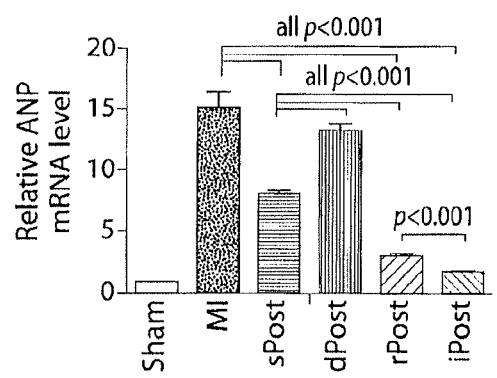
FIG. 7E is a bar graph showing the mRNA expression of ANP wherein data are expressed as mean±SD, with the same abbreviations as above.

Going along with this, the average cross-sectional area (CSA) of cardiac myocytes decreased in dose-dependent fashion (FIGS. 7A,B). Quantification of hypertrophy-related genes expression showed that increased gene expression of ANP and β-MHC was attenuated while the decrease in expression of α-MHC was recovered by rIPost, again in a dosage dependent fashion (FIGS. 7C-E). However, the effects were absent when the maneuver was delayed to 72 hours after reperfusion (FIGS. 7A-E).

Improved Cardiac Geometry, Function and Hemodynamic Parameters. On day 28, MI rats demonstrated significant LV dilation, as evidenced by increases in LVEDD compared with sham rats ($p<0.05$, table). This geometric change was accompanied by decrease in FS compared with sham rats ($p<0.05$, table). While sPost significantly improved adverse LV remodeling, reflected by a decrease in LVEDD and an increase in FS compared with MI rats ($p<0.05$, respectively. Table), rIPost therapy resulted in a further improvement in LV chamber size and function, with the greatest effects achieved by iPost in comparison with rPost ($p<0.05$, respectively). Hemodynamic analysis demonstrated the same pattern of benefits from rIPost, in a dose-dependent manner compared with MI and dPost (Table).

Discussion

This is the first study to demonstrate that remote conditioning improves late LV remodeling and survival in a dose dependent manner. The data show that a single early episode of remote per-conditioning, initiated during the final 20 minutes of ischemia and continuing into the reperfusion period, can afford long term protection against LV remodeling after MI, as evidence by attenuated LV dilation and improved cardiac function, and less myocardial hypertrophy and fibrosis. This effect is lost, if the stimulus is delayed to day 4, with animals in this group being indistinguishable from those in the MI group, who did not receive rIPost. Interestingly, when additional repeated rIPost was given during the first 28 days after infarction, no further decrease in infarct size was detected, however, there was additional protection against adverse LV remodeling, which was closely associated with attenuated inflammatory responses, and less oxidative stress, compared to those having a single early episode of post-conditioning. Furthermore, the protective effect of repeated rIPost was demonstrably dose-dependent, with significant additional benefits from daily rIPost therapy when compared to rIPost delivered every 3 days during the 28 follow up period. These functional benefits translated to improved survival at 84 days, again with maximal benefit seen in the group subjected to daily post-conditioning for the first 28 days.

Ischemia reperfusion injury leads to excessive production of reactive oxygen species (ROS) as well as decreased antioxidant activity [23]. ROS generated upon reperfusion causes cellular damage with oxidation and peroxidation of membrane lipids with consequent "ROS induced ROS generation" [24] setting the scene for a cascade of local inflammatory processes that contribute to further cellular injury during the days and weeks after an ischemia-reperfusion injury. Since the phenomenon of ischemic pre-conditioning was first described by Murry et al. [25] extensive studies have been performed to elucidate the underlying mechanisms by which pre and post-conditioning exert their cardioprotective effects. While the exact mechanisms are still not fully understood, it is generally agreed that the attenuation of ROS generation [26-28] is of paramount importance in the protection afforded by these strategies. Furthermore, it is well established that continued ROS generation and inflammation is also pivotal in the process of post MI remodeling [29,30]. Remote pre-, per- and post-conditioning induced by limb ischemia have all been demonstrated to provide potent acute protection against myocardial damage in experimental models [5,14,15] and in clinical trials [31]. There also seems to be an effect on circulating monocytes, downregulating white cell proinflammatory pathways [21,32] and, when delivered daily for 10 days, reducing neutrophil adhesion phagocytosis and proinflammatory cytokine responses. Our findings are consistent with reduced oxidative stress (reduced NF-kB phosphorylation and activation of TGFβ1/Smad2 signaling), decreased inflammatory cell migration into the infarct zone (observed directly and as attenuated MDA concentration and 8-OHdG immunostaining density) and reduced local inflammatory cytokine signaling (reduced tissue MCP-1 expression, reduced circulating TNF-α and IL-1β levels). The modification of the local and circulating inflammatory milleau is likely crucial to the chronic effects of chronic rIPost. Local chemokines such as MCP-1 are responsible for inducing recruitment of mononuclear cells. Moreover, activated NF-κB pathways can also up-regulate the target gene expression of TNF-α and IL-1β[29,30,33]. This 'anti-inflammatory' effect is over and above infarct size reduction, as there was no additional benefit of repeated post-conditioning compared with perconditioning alone in our studies. Clearly more focused experiments will be required to assess any causal relationship between rIPost, local oxidative stress and circulating cellular responses, but the overall effect of this stimulus, when repeated during the first 28 days after our experimental insult, to improve remodeling in the form of LV dilation and dysfunction in combination with myocyte hypertrophy has obvious clinical relevance to post-MI recovery in humans.

In this regard, and similar to other remote conditioning protocols, there is capacity for our observations to translate rapidly to clinical trials. The facile nature of the remote stimulus by transient limb ischemia has already led to positive clinical trials showing benefits of remote pre-conditioning in adults and children undergoing cardiac and vascular surgery[7]. Furthermore, the results of a RCT of perconditioning in adults with evolving MI (4 cycles of 5 minutes transient limb ischemia followed by 5 minutes reperfusion prior to emergency PCI) were recently reported in abstract form [34]. The early conditioning stimulus used in the current study is somewhat of a hybrid of perconditioning and post-conditioning, as the conditioning stimulus started during ischemia, and continued during the early reperfusion period. As such, it perhaps better reflects a "real-life" period, but extends into the reperfusion period after successful PCI. Whether the subsequent conditioning episodes are best described as post-conditioning or pre-conditioning is largely semantic, but we would caution that very little is known of the effects of chronic ischemic conditioning under any circumstances. Consequently, any clinical trial must include vigilant assessment for adverse, as well as beneficial effects of chronic rIPost strategies.

CONCLUSION

In summary, we have shown that compared with a single episode of remote perconditioning, chronic administration of remote ischemic post-conditioning provides additional protection against pathological ventricular remodeling which is independent of the effects on infarct size, and improves survival, after MI. This dose-dependent protection conferred was associated with improved oxidative stress, inflammatory response and modulation of hypertrophic and fibrotic signaling.

REFERENCES

1. Bolognese L, Neskovic A N, Parodi G, Santoro G M, Buonamici P, Cerisano G, Antoniucci Dl. Impact of microvascular dysfunction on left ventricular remodeling and long-term clinical outcome after primary coronary angioplasty for acute myocardial infarction. Circulation. 2004; 109(9):1121-1126
2. Lewis E F, Moye L A, Rouleau J L, Sacks F M, Arnold J M, Warnica J W, Flaker G C, Braunwald E, Pfeffer M A; CARE Study. Predictors of late development of heart failure in stable survivors of myocardial infarction: the CARE study. J Am Coll Cardiol. 2003; 42(8):1446-1453.
3. Nian M, Lee P, Khaper N, Liu P. Inflammatory cytokines and postmyocardial infarction remodeling. Circ Res. 2004 (12); 94:1543-1553.
4. Sun Y. Myocardial repair/remodelling following infarction: roles of local factors. Cardiovasc Res. 2009; 81(3): 482-90.
5. Konstantinov I E, Li J, Stokoe J, Shimizu M, Kharbanda R K, Redington A N. Remote ischemic pre-conditioning of the recipient reduces myocardial ischemia-reperfusion injury of the denervated donor heart via a Katp channel-dependent mechanism. Transplantation. 2005; 79(12): 1691-1695.

6. Kerendi F, Kin H, Halkos M E, Jiang R, Zatta A J, Zhao Z Q, Guyton R A, Vinten-Johansen J. Remote post-conditioning. Brief renal ischemia and reperfusion applied before coronary artery reperfusion reduces myocardial infarct size via endogenous activation of adenosine receptors. Basic Res Cardiol. 2005; 100(5):404-412.
7. Cheung M M, Kharbanda R, Konstantinov I E, Shimizu M, Frndova H, Li J, Holtby H M, Cox P N, Smallhorn J F, Van Arsdell G S, Redington A N. Randomized controlled trial of the effects of remote ischemic pre-conditioning on children undergoing cardiac surgery: first clinical application in humans. J Am Coll Cardiol. 2006; 47(11):2277-82.
8. Hausenloy D J, Mwamure P K, Venugopal V, Harris J, Barnard M, Grundy E, Ashley E, Vichare S, Di Salvo C, Kolvekar S, Hayward M, Keogh B, MacAllister R J, Yellon D M. Effect of remote ischaemic pre-conditioning on myocardial injury in patients undergoing coronary artery bypass graft surgery: a randomized controlled trial. Lancet. 2007; 370(9587):575-79.
9. Hoole S P, Heck P M, Sharples L, Khan S N, Duehmke R, Densem C G, Clarke S C, Shapiro L M, Schofield P M, O'Sullivan M, Dutka D P. Cardiac remote ischemic pre-conditioning in coronary stenting (CRISP stent) study: a prospective, randomized control trial. Circulation 2009; 119(6):820-7.
10. Przyklenk K, Bauer B, Ovize M, Kloner R A, Whittaker P. Regional ischemic 'pre-conditioning' protects remote virgin myocardium from subsequent sustained coronary occlusion. Circulation 1993; 87(3):893-9.
11. Gho B C, Schoemaker R G, van den Doel M A, Duncker D J, Verdouw P D. Myocardial protection by brief ischemia in noncardiac tissue. Circulation 1996; 94(9):2193-200.
12. Takaoka A, Nakae I, Mitsunami K, Yabe T, Morikawa S, Inubushi T, Kinoshita M. Renal ischemia/reperfusion remotely improves myocardial energy metabolism during myocardial ischemia via adenosine receptors in rabbits: effects of "remote pre-conditioning". J Am Coll Cardiol. 1999; 33(2): 556-64.
13. Heidbreder M, Naumann A, Tempel K, Dominiak P, Dendorfer A. Remote vs. ischaemic pre-conditioning: the differential role of mitogen-activated protein kinase pathways. Cardiovasc Res. 2008; 78(1):108-15.
14. Kharbanda R K, Mortensen U M, White P A, Kristiansen S B, Schmidt M R, Hoschtitzky J A, Vogel M, Sorensen K, Redington A N, MacAllister R. Transient limb ischemia induces remote ischemic pre-conditioning in vivo. Circulation. 2002; 106(23):2881-2883.
15. Schmidt M R, Smerup M, Konstantinov I E, Shimizu J, Li J, Cheung M, White P A, Kristiansen S B, Sorensen K, Dzavik V, Redington A N, Kharbanda R K. Intermittent peripheral tissue ischemia during coronary ischemia reduces myocardial infarction through a KATP-dependent mechanism: first demonstration of remote ischemic per-conditioning. Am J Physiol Heart Circ Physiol. 2007; 292(4):H1883-90.
16. Zhao Z Q, Corvera J S, Halkos M E, Kerendi F, Wang N P, Guyton R A, Vinten-Johansen J. Inhibition of myocardial injury by ischemic post-conditioning during reperfusion: comparison with ischemic pre-conditioning. Am J Physiol Heart Circ Physiol. 2003; 285(2):H579-88
17. Vinten-Johansen J, Yellon D M, Opie L H. Post-conditioning: a simple, clinically applicable procedure to improve revascularization in acute myocardial infarction. Circulation. 2005; 112(14):2085-8.
18. Gritsopoulos G, Iliodromitis E K, Zoga A, Farmakis D, Demerouti E, Papalois A, Paraskevaidis I A, Kremastinos DT1. Remote post-conditioning is more potent than classic post-conditioning in reducing the infarct size in anesthetized rabbits. Cardiovasc Drugs Ther. 2009; 23(3):193-8.
19. Fukuda S, Kaga S, Sasaki H, Zhan L, Zhu L, Otani H, Kalfin R, Das D K, Maulik N. Angiogenic signal triggered by ischemic stress induces myocardial repair in rat during chronic infarction. J Mol Cell Cardiol. 2004; 36(4):547-59.
20. Dairaku Y, Miura T, Harada N, Kimura M, Okamura T, Iwamoto H, Kametani R, Yamada M, Ikeda Y, Iwatate M, Kawamura S, Matsuzaki M. Effect of ischemic pre-conditioning and mitochondrial KATP channel openers on chronic left ventricular remodeling in the ischemic-reperfused rat heart. Circ J. 2002; 66(4):411-5.
21. Shimizu M, Saxena P, Konstantinov I E, Cherepanov V, Cheung M M, Wearden P, Hua Z, Schmidt M, Downey G P, Redington A N. Remote Ischemic pre-conditioning decreases adhesion and selectively modifies functional responses of human neutrophils. J Surg Res. 2008; Nov. 12. [Epub ahead of print]
22. Pfeffer M A, Pfeffer J M, Fishbein M C, Fletcher P J, Spadaro J, Kloner R A, Braunwald E. Myocardial infarct size and ventricular function in rats. Circ Res. 1979; 44(4):503-12.
23. Hill M F, Singal P K. Antioxidant and oxidative stress changes during heart failure subsequent to myocardial infarction in rats. Am J Pathol. 1996; 148(1):291-300.
24. Zorov D B, Juhaszova M, Sollott S J. Mitochondrial ROS-induced ROS release: an update and review. Biochim Biophys Acta. 2006; 1757(5-6):509-17.
25. Murry C E, Jennings R B, Reimer K A. Pre-conditioning with ischemia: a delay of lethal cell injury in ischemic myocardium. Circulation. 1986; 74(5):1124-36.
26. Baines C P, Goto M, Downey J M. Oxygen radicals released during ischemic pre-conditioning contribute to cardioprotection in the rabbit myocardium. J Mol Cell Cardiol 1997; 29(1):207-216.
27. Chen W, Gabel S, Steenbergen C, Murphy E. A redox based mechanism for cardioprotection induced by ischemic pre-conditioning in perfused rat heart. Circ Res. 1995; 77:424-429.
28. Tritto I, D'Andrea D, Eramo N, Scognamiglio A, De Simone C, Violante A, Esposito A, Chiariello M, Ambrosio G. Oxygen radicals can induce pre-conditioning in rabbit hearts. Circ Res. 1997; 80(5):743-8.
29. Frangogiannis N G, Smith C W, Entman M L. The inflammatory response in myocardial infarction. Circulation. 2002; 53(1):31-47.
30. Hori M, Nishida K. Oxidative stress and left ventricular remodeling after myocardial infarction. Cardiovascular Res. 2009; 81:457-464.
31. Loukogeorgakis S P, Williams R, Panagiotidou A T, Kolvekar S K, Donald A, Cole T J, Yellon D M, Deanfield J E, MacAllister R J. Transient limb ischemia induces remote pre-conditioning and remote post-conditioning in humans by a K(ATP)-channel dependent mechanism. Circulation 2007; 116:1386-95.
32. Konstantinov I E, Arab S, Kharbanda R K, Li J, Cheung M M, Cherepanov V, Downey G P, Liu P P, Cukerman E, Coles J G, Redington A N. The remote ischemic pre-conditioning stimulus modifies inflammatory gene expression in humans. Physiol Genomics. 2004; 19(1): 143-50.
33. Kabe Y, Ando K, Hirao S, et al. Redox regulation of NF-kappaB activation: distinct redox regulation between the cytoplasm and the nucleus. Antiox Redox Signal. 2005; 7:395-403.

34. Kharbanda R K, Nielsen T T, Redington A N. Translation of remote ischaemic pre-conditioning into clinical practice. Lancet. 2009; 374(9700):1557-1565.

EQUIVALENTS

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

TABLE 1

Data obtained from each group rats to assess cardiac geometry, function, infarct size and hemodynamic changes.

| | | | IR | | | |
|---|---|---|---|---|---|---|
| Parameter | Sham | MI | sPost | dPost | rPost | iPost |
| Motality (dead rats/total number of rats underwent reperfusion injury) | | | | | | |
| Day 4 | 0/21 | 6/28 | 3/24 | 5/26 | 3/23 | 2/22 |
| Day 28 | 0/21 | 9/28 | 4/24 | 8/26 | 3/23 | 2/22 |

TABLE 1-continued

Data obtained from each group rats to assess cardiac geometry, function, infarct size and hemodynamic changes.

| | | | IR | | | |
|---|---|---|---|---|---|---|
| Parameter | Sham | MI | sPost | dPost | rPost | iPost |
| Echocardiographic data | | | | | | |
| LVEDD (cm) | 0.54 ± 0.13 | 0.74 ± 0.07* | 0.63 ± 0.07# | 0.67 ± 0.09* | 0.57 ± 0.07# | 0.53 ± 0.07*& |
| LVESD (cm) | 0.23 ± 0.06 | 0.53 ± 0.07* | 0.40 ± 0.05*# | 0.46 ± 0.05*# | 0.34 ± 0.04*# | 0.29 ± 0.04*#& |
| FS (%) | 57 ± 3 | 29 ± 3* | 36 ± 7*# | 31 ± 3*& | 40 ± 3*# | 45 ± 3*#&% |
| Hemodynamic data | | | | | | |
| HR (bpm) | 404 ± 26 | 394 ± 22 | 402 ± 25 | 410 ± 23 | 405 ± 23 | 401 ± 25 |
| LVEDP (mmHg) | 5.08 ± 0.61 | 19.45 ± 1.29* | 14.03 ± 0.87*# | 18.42 ± 1.3*& | 12.96 ± 0.65*#& | 11.17 ± 0.84*#&% |
| dP/dt$_{max}$ (mmHg/s) | 5815 ± 253 | 2405 ± 347* | 3247 ± 227*# | 2612 ± 335*& | 4038 ± 284*#& | 4519 ± 278*#&% |
| dP/dt$_{min}$ (mmHg/s) | 5043 ± 309 | 2117 ± 164* | 2777 ± 246*# | 2418 ± 360*& | 3328 ± 240*#& | 3855 ± 270*#&% |
| Morphology data | | | | | | |
| LVMI (mg/g) | 2.08 ± 0.34 | 3.25 ± 0.54* | 2.73 ± 0.31*# | 3.01 ± 0.36* | 2.51 ± 0.32*# | 2.18 ± 0.28*# |
| Infarct size | | | | | | |
| NA/AAR (%) (day 4) | 0 | 50.5 ± 4.11 | 35.63 ± 4.21# | 48.13 ± 4.7 | 33.88 ± 3.52# | 31.88 ± 4.82# |
| IP (%) (day 28) | 0 | 44.63 ± 3.66 | 29.27 ± 3.01# | 42 ± 4.54 | 28.5 ± 3.46# | 26.25 ± 4.43# |

All the data are expressed as mean ± SD.
*denotes $P < 0.05$ vs Sham group;
$P < 0.05$ vs MI group;
&$P < 0.05$ vs sPost group;
%$P < 0.05$ vs rPost group;
LVEDD, left ventricular end-diastolic diameter;
LVESD, left ventricular end-systolic diameter;
LVEDP, left ventricular end-diastolic pressure;
LV, left ventricle; and
BW, body weight.

What is claimed is:

1. A method for reducing the incidence, delaying the onset, and/or reducing the severity of heart dysfunction and/or failure following a myocardial infarction comprising:
performing repeated remote ischemic conditioning (RIC) regimens on a subject beginning after an ischemic phase and a reperfusion phase of the myocardial infarction and continuing for at least three days.

2. The method of claim 1, wherein the repeated RIC regimens are commenced within 1 week after the myocardial infarction occurs.

3. The method of claim 1, wherein the repeated RIC regimens are performed every two days.

4. The method of claim 1, wherein the repeated RIC regimens are performed daily.

5. The method of claim 1, wherein the repeated RIC regimens are commenced within a month after the myocardial infarction occurs.

6. The method of claim 1, wherein the repeated RIC regimens are performed more than once per day on one or more days.

7. The method of claim 1, wherein the subject has not undergone balloon angioplasty or a stent placement.

8. The method of claim 1, wherein each RIC regimen comprises at least four cycles, each cycle comprising blood flow occlusion and reperfusion.

9. The method of claim 1, wherein each RIC regimen comprises more than one cycle, and each cycle comprises about 5 minutes of occlusion and 5 minutes of reperfusion.

10. The method of claim 9, wherein occlusion is created by a pressure that is at least 15 mmHg above systolic pressure.

11. The method of claim 1, wherein each RIC regimen is performed at the same site.

12. The method of claim 11, wherein each RIC regimen is performed on an upper limb of the subject.

13. The method of claim 1, further comprising administering to the subject an angiotensin-converting enzyme (ACE) inhibitor.

14. The method of claim 1, further comprising administering to the subject an angiotensin II receptor blocker.

15. The method of claim 1, further comprising administering to the subject an anti-platelet therapy.

16. The method of claim 1, wherein 2, 3, 4, 5 or more RIC regimens are performed on a subject in a single day.

17. The method of claim 1, wherein the repeated RIC regimens are performed for at least 28 days after the myocardial infarction.

18. The method of claim 17, wherein the repeated RIC regimens are performed for a period of one month, two months, three months, four months, five months, six months, seven months, eight months, nine months, ten months, or twelve months after the myocardial infarction occurs.

19. The method of claim 18, wherein the repeated RIC regimens are performed for a remaining lifespan of the subject.

20. The method of claim 1, wherein the repeated RIC regimens are commenced at least 12 hours after the myocardial infarction occurs.

21. The method of claim 1, wherein the repeated RIC regimens are commenced at least 6 hours after the myocardial infarction occurs.

22. The method of claim 1, wherein the repeated RIC regimens are commenced at least 24 hours after the myocardial infarction.

23. The method of claim 1, wherein the repeated RIC regimens are commenced at least 36 hours after the myocardial infarction occurs.

24. The method of claim 1, wherein adverse remodeling of a left ventricle of a heart of the subject is restricted.

25. A method for restricting adverse remodeling of a left ventricle of a heart of a subject following a myocardial infarction comprising performing repeated remote ischemic conditioning (RIC) regimens on the subject beginning after an ischemic phase and a reperfusion phase of the myocardial infarction and continuing at least daily for one or more days, the repeated RIC regimens being commenced within thirty days after the myocardial infarction occurs.

* * * * *